US011602579B2

(12) United States Patent
Dufrane

(10) Patent No.: US 11,602,579 B2
(45) Date of Patent: Mar. 14, 2023

(54) BIOMATERIAL COMPRISING ADIPOSE-DERIVED STEM CELLS AND METHOD FOR PRODUCING THE SAME

(71) Applicant: NOVADIP BIOSCIENCES, Mont-Saint-Guibert (BE)

(72) Inventor: Denis Dufrane, Lasne (BE)

(73) Assignee: NOVADIP BIOSCIENCES, Mout-Saint-Guibert (BE)

( * ) Notice: Subject to any disclaimer, the term of this patent is extended or adjusted under 35 U.S.C. 154(b) by 0 days.

(21) Appl. No.: 16/137,396

(22) Filed: Sep. 20, 2018

(65) Prior Publication Data
US 2019/0083680 A1    Mar. 21, 2019

Related U.S. Application Data

(60) Provisional application No. 62/561,046, filed on Sep. 20, 2017.

(51) Int. Cl.
| | |
|---|---|
| A61K 35/28 | (2015.01) |
| A61K 38/30 | (2006.01) |
| A61L 27/36 | (2006.01) |
| A61L 27/10 | (2006.01) |
| A61K 38/18 | (2006.01) |
| A61P 19/08 | (2006.01) |
| A61K 38/19 | (2006.01) |
| A61L 27/12 | (2006.01) |
| A61L 27/54 | (2006.01) |
| C12N 5/077 | (2010.01) |
| A61L 27/38 | (2006.01) |
| A61K 38/17 | (2006.01) |
| A61L 27/46 | (2006.01) |

(52) U.S. Cl.
CPC ............ *A61L 27/365* (2013.01); *A61K 35/28* (2013.01); *A61K 38/1793* (2013.01); *A61K 38/1866* (2013.01); *A61K 38/191* (2013.01); *A61K 38/195* (2013.01); *A61K 38/30* (2013.01); *A61L 27/10* (2013.01); *A61L 27/12* (2013.01); *A61L 27/3633* (2013.01); *A61L 27/3834* (2013.01); *A61L 27/46* (2013.01); *A61L 27/54* (2013.01); *A61P 19/08* (2018.01); *C12N 5/0654* (2013.01); *A61L 2300/414* (2013.01); *C12N 2506/1384* (2013.01); *C12N 2513/00* (2013.01); *C12N 2533/14* (2013.01); *C12N 2533/18* (2013.01); *C12N 2533/90* (2013.01)

(58) Field of Classification Search
CPC ............................ A61K 35/28; A61K 38/1866
See application file for complete search history.

(56) References Cited

U.S. PATENT DOCUMENTS

| | | | |
|---|---|---|---|
| 9,427,491 B2 * | 8/2016 | Xu | ........... A61L 24/02 |
| 2008/0033572 A1 | 2/2008 | D'Antonio et al. | |
| 2010/0080836 A1 * | 4/2010 | Busch | .................. C12N 5/0654 |
| | | | 424/422 |
| 2011/0104230 A1 | 5/2011 | Mousa et al. | |

FOREIGN PATENT DOCUMENTS

| | | |
|---|---|---|
| EP | 3090764 A1 | 11/2016 |
| WO | 2006062989 A1 | 6/2006 |
| WO | 2009125402 A2 | 10/2009 |
| WO | 2010059565 A2 | 5/2010 |
| WO | 2013059089 A1 | 4/2013 |
| WO | WO-2016161944 A1 * | 10/2016 ............. A61L 27/44 |

OTHER PUBLICATIONS

Sart et al., "Three-Dimensional Aggregates of Mesenchymal Stem Cells: Cellular Mechanisms, Biological Properties, and Applications", Tissue Engineering: Part B, published online 2013, vol. 20, No. 5, pp. 365-380. (Year: 2013).*
Nakagawa et al., "��-Tricalcium Phosphate Micron Particles Enhance Calcification of Human Mesenchymal Stem Cells In Vitro", Journal of Nanomaterials, 2013, vol. 2013, Article ID 426786, pp. 1-13. (Year: 2013).*
Bruderer M et al, "Role and regulation of RUNX2 in osteogenesis" Eur Cell Mater, 2014, 28:269-286.
Xu J et al, "Potential mechanisms underlying the Runx2 induced osteogenesis of bone marrow mesenchymal stem cells" Am J Trans Res, 2015, 7(12):2527-35.
Johnson D et al, "Expression of CRYP-alpha, LAR, PTP-delta, and PTP-rho in the developing Xenopus visual system" Mech Dev. 2000, 92(2):291-4.
Rice et al., "Integration of FGF and TWIST in calvarial bone and suture development" Development. 2000, 127(9):1845-1855.
Fagiani E et al, "Angiopoietins in angiogenesis" Cancer Lett, 2013, 328(1):18-26.
Pasquale, "Eph receptor signalling casts a wide net on cell behaviour" Nat Rev Mol Cell Biol, 2005, 6(6):462-475.
Hu K et al, "The roles of vascular endothelial growth factor in bone repair and regeneration" Bone, 2016, 91:30-38.
Murakami M et al, "Fibroblast growth factor regulation of neovascularization" Curr Opin Hematol. 2008, 15(3):215-220.
Bouloumie A et al, "Leptin, the product of Ob gene, promotes angiogenesis" Circ. Res. 1998, 83(10):1059-1066.
Sierra-Honigmann MR et al, "Biological action of leptin as an angiogenic factor" Science. 1998, 281(5383):1683-1686.
Madrigal M et al., "A review of therapeutic effects of mesenchymal stem cell secretions and induction of secretory modification by different culture methods" J Transl Med. 2014, 12:260.

(Continued)

*Primary Examiner* — Laura Schuberg
(74) *Attorney, Agent, or Firm* — Jerold I. Schneider; Schneider IP Law

(57) ABSTRACT

The present invention relates to a biomaterial comprising adipose-derived stem cells (ASCs), a ceramic material and an extracellular matrix. In particular, the biomaterial according the present invention secretes osteoprotegerin (OPG), and comprises insulin-like growth factor (IGF1) and stromal cell-derived factor 1-alpha (SDF-1α). The present invention also relates to methods for producing the biomaterial and uses thereof.

10 Claims, 14 Drawing Sheets

(56) References Cited

OTHER PUBLICATIONS

Ahluwalia A et al., "Critical role of hypoxia sensor—HIF-1α in VEGF gene activation. Implications for angiogenesis and tissue injury healing" Curr Med Chem. 2012, 19(1):90-97.
Hawkins KE et al., "The role of hypoxia in stem cell potency and differentiation" Regen Med. 2013, 8(6):771-782.
Youn SW et al., "COMP-Ang1 stimulates HIF-1α-mediated SDF-1 overexpression and recovers ischemic injury through BM-derived progenitor cell recruitment" Blood. 2011, 117:4376-4386.
Ceradini DJ et al., "Progenitor cell trafficking is regulated by hypoxic gradients through HIF-1 induction of SDF-1" Mat Med. 2004, 10(8):858-864.
Schubert et al. "The enhanced performance of bone allografts using osteogenic-differentiated adipose-derived mesenchymal stem cells" Biomaterials, 2011, 32(34):8880-91.
Saxer et al., "Implantation of Stromal Vascular Fraction Progenitors at Bone Fracture Sites: From a Rat Model to a First-in-Man Study" Stem Cells. 2016, 34(12):2956-2966.
Manassero et al., "Establishment of a Segmental Femoral Critical-size Defect Model in Mice Stabilized by Plate Osteosynthesis" Journal of Visualized Experiments. 2016, (116): 52940.
Wang et al., "Effect of regional gene therapy with bone morphogenetic protein-2-producing bone marrow cells on spinal fusion in rats" J. Bone and Joint Surg. 2003, 85-A(5):905-911.
Belill et al., "Femoral strength after induced lesions in rats (*Rattus norvegicus*)" Comp. Med. 2014, 61(3):186-192.
Aguilar et al., "Murine but not human mesenchymal stem cells generate osteosarcoma-like lesions in the lung" Stem Cells. 2007, 25(6):1586-1594.
Bernardo et al., "Human bone marrow derived mesenchymal stem cells do not undergo transformation after long-term in vitro culture and do not exhibit telomere maintenance mechanisms" Cancer Res. 2007, 67(19):9142-9149.
Xiao et al., "Mesenchymal stem cell transformation and sarcoma genesis" Clin. Sarcoma Res. 2013, 3(1):10.
Tarte et al., "Clinical-grade production of human mesenchymal stromal cells: occurrence of aneuploidy without transformation" Blood. 2010, 115(8):1549-1553.
Cooper et al., "A copy number variation morbidity map of developmental delay" Nat. Genetics. 2011, 43(9):838-846.
Slavotinek. A.M., "Novel microdeletion syndromes detected by chromosome microarrays" Hum. Genetics. 2008, 124(1): 1-17.
Barkholt et al., "Risk of tumorigenicity in mesenchymal stromal cell-based therapies-bridging scientific observations and regulatory viewpoints" Cytotherapy. 2013, 15(7):753-759.
Dufrane et al., "Scaffold-free Three-dimensional Graft From Autologous Adipose-derived Stem Cells for Large Bone Defect Reconstruction Clinical Proof of Concept", Medicine (Hagerstown), 2015, vol. 94, No. 50.
Fomekong et al., "Application of a three-dimensional graft of autologous osteodifferentiated adipose stem cells in patients undergoing minimally invasive transforaminal lumbar interbody fusion: clinical proof of concept.", Acta Neurochirurgica, 2017, vol. 159, No. 3, pp. 527-536.
Schubert et al., "Critical size bone defect reconstruction by an autologous 3D osteogenic-like tissue derived from differentiated adipose MSCs", Biomaterials, Elsevier Science Publishers, 2013, vol. 34, No. 18, pp. 4428-4438.
Dufrane et al., "A Simple Method to Determine the Purity of Adipose-Derived Stem Cell-Based Cell Therapies.", Stem Cells Translational Medicine, 2016, vol. 5, No. 11, pp. 1575-1579.
International Search Report of International Application No. PCT/EP2018/075545, dated Oct. 19, 2018.
European Search Report of application EP 18 165 933.5, date of completion Jun. 13, 2018.

* cited by examiner

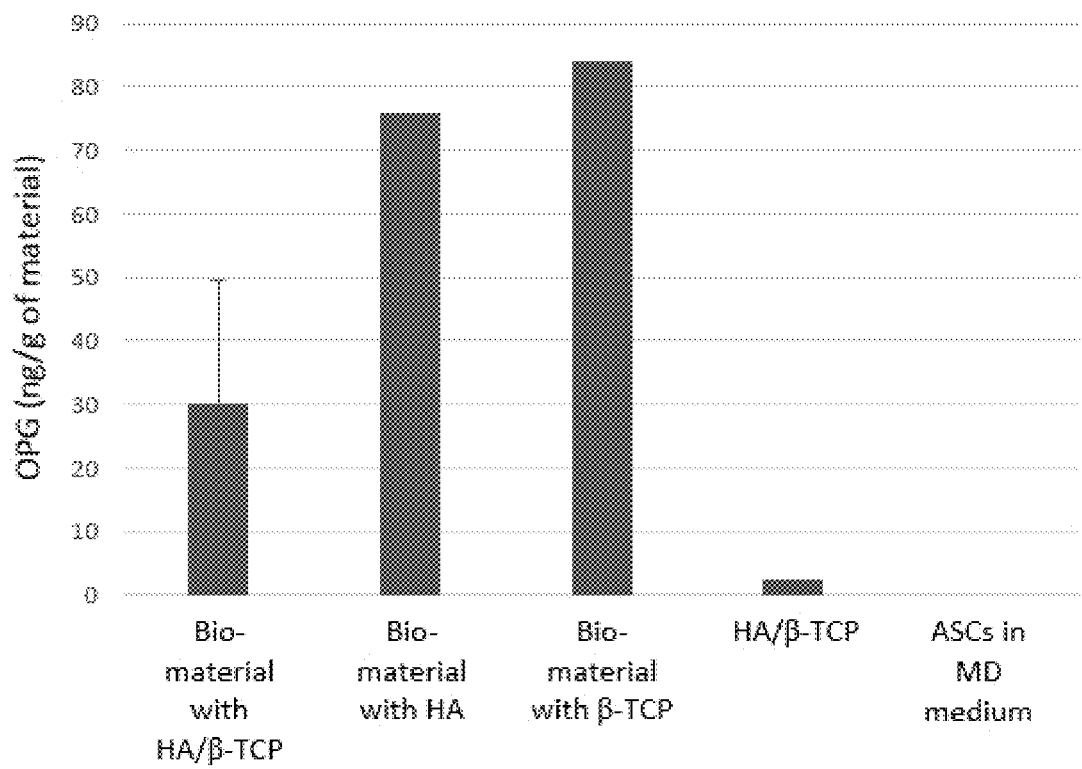
FIG. 8
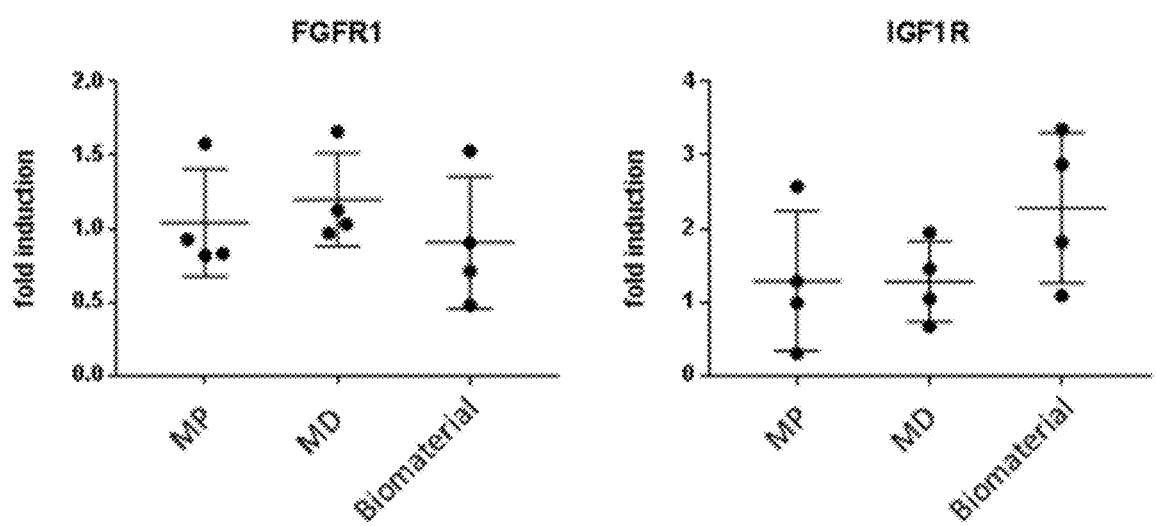
FIG. 9A
FIG. 9B

FIG. 11A
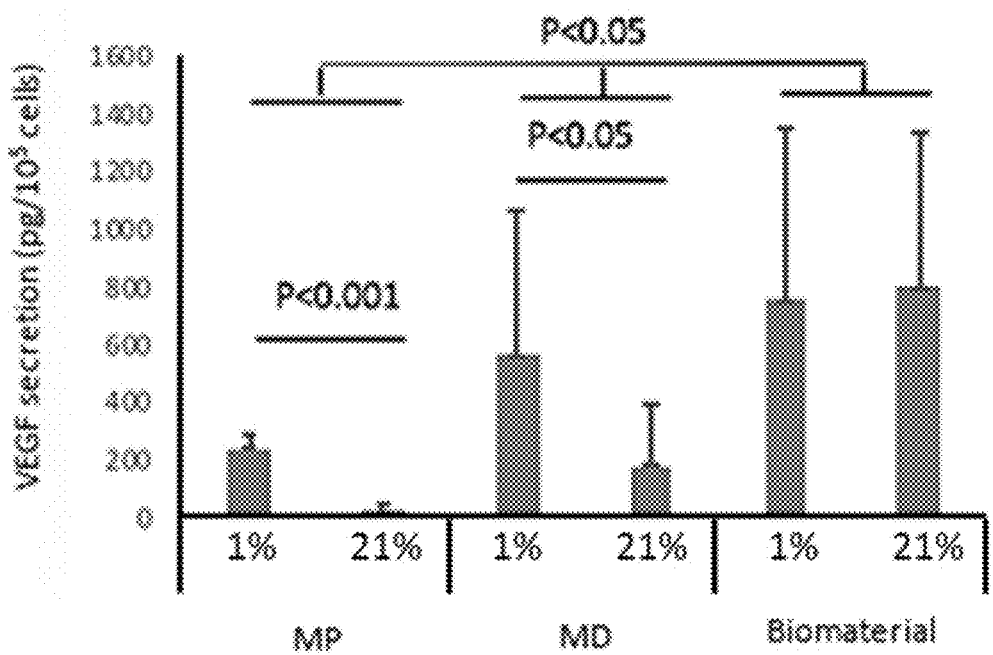
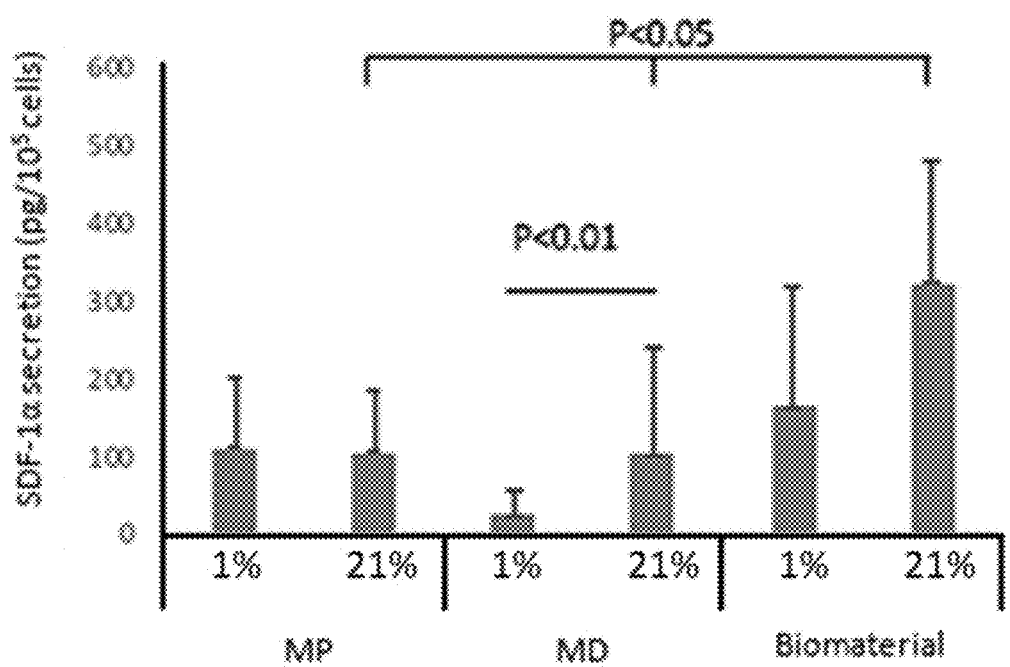
FIG. 11B

BIOMATERIAL COMPRISING ADIPOSE-DERIVED STEM CELLS AND METHOD FOR PRODUCING THE SAME

RELATED APPLICATIONS

This application claims priority to U.S. Provisional Patent Application No. 62/561,046, filed Sep. 20, 2017, the contents of which are incorporated herein by reference.

FIELD OF INVENTION

The present invention relates to the field of stem cells and their use for the production of multi-dimensional biomaterials. In particular, the present invention relates to biomaterials comprising adipose-derived stem cells (ASCs), as well as methods for preparing and using such biomaterials for therapy.

BACKGROUND

Bone defect is a lack of bone tissue in a body area, where bone should normally be. Bone defects can be treated by various surgical methods. However, often there are factors that impair bone healing, like diabetes mellitus, immunosuppressive therapy, poor locomotor status and others that one has to take into account when a procedure is planned.

Surgical methods of bone defect reconstruction include inter alia decortication, excision and fixation, cancellous bone grafting and the Ilizarov intercalary bone transport method. However, patients commonly have prolonged ambulatory impairment with suboptimal functional and aesthetic results.

Tissue engineering involves the restoration of tissue structure or function through the use of living cells. The general process consists of cell isolation and proliferation, followed by a re-implantation procedure in which a scaffold material is used. Mesenchymal stem cells (MSCs) provide a good alternative to cells from mature tissue and have a number of advantages as a cell source for bone and cartilage tissue regeneration.

By definition, a stem cell is characterized by its ability to undergo self-renewal and its ability to undergo multilineage differentiation and form terminally differentiated cells. Ideally, a stem cell for regenerative medicinal applications should meet the following set of criteria: (i) should be found in abundant quantities (millions to billions of cells); (ii) can be collected and harvested by a minimally invasive procedure; (iii) can be differentiated along multiple cell lineage pathways in a reproducible manner; (iv) can be safely and effectively transplanted to either an autologous or allogeneic host.

Studies have demonstrated that stem cells have the capacity to differentiate into cells of mesodermal, endodermal and ectodermal origins. The plasticity of MSCs most often refers to the inherent ability retained within stem cells to cross lineage barriers and to adopt the phenotypic, biochemical and functional properties of cells unique to other tissues. Adult mesenchymal stem cells can be isolated from bone marrow and adipose tissue, for example.

Adipose-derived stem cells are multipotent and have profound regenerative capacities. The following terms have been used to identify the same adipose tissue cell population: Adipose-derived Stem/Stromal Cells (ASCs); Adipose Derived Adult Stem (ADAS) Cells, Adipose Derived Adult Stromal Cells, Adipose Derived Stromal Cells (ADSC), Adipose Stromal Cells (ASC), Adipose Mesenchymal Stem Cells (AdMSC), Lipoblasts, Pericytes, Pre-Adipocytes, Processed Lipoaspirate (PLA) Cells. The use of this diverse nomenclature has led to significant confusion in the literature. To address this issue, the International Fat Applied Technology Society reached a consensus to adopt the term "Adipose-derived Stem Cells" (ASCs) to identify the isolated, plastic-adherent, multipotent cell population.

Osteogenic differentiated ASCs were shown to have a great healing potential in various preclinical models when seeded on various scaffolds, such as β-tricalcium phosphate (β-TCP), hydroxyapatite (HA), type I collagen, poly-lactic-co-glycolic acid (PLGA) and alginate. The international patent application WO2013/059089 relates to a bone paste comprising stem cells and a mixture of calcium phosphate cement such as tricalcium phosphate and hydroxyapatite. US2011/104230 discloses a bone patch comprising scaffold material comprising synthetic ceramic material, mesenchymal stem cells and signaling molecules.

However, despite encouraging results in small animal models, critical size bone reconstruction using ASCs loaded on scaffolds remains limited by the large size of bone defect and consequently by the size of the implant to engineer. The cellular engraftment of the seeded cells is also limited by the poor diffusion of oxygen and nutrients. In addition, the cellular position within the scaffold is a major limitation for their in vitro and in vivo survival. Bioreactors with flow perfusion of scaffolds were designed to improve cell migration within the implant for a more homogenous cellular distribution, cell survival by delivering oxygen and nutrients to the core of the implant, and osteogenic cell differentiation (by the fluid shear force). Although these techniques are promising, relevant pre- and clinical data in large animal models are limited.

There is thus still a need in the art for tissue engineered materials for bone tissue regeneration that are fully biocompatible and provide appropriate mechanical features for the designated applications. Therefore, the present invention relates to a graft made of ASCs differentiated in a multi-dimensional osteogenic structure with ceramic material.

BRIEF SUMMARY

The present invention relates to a multi-dimensional biomaterial comprising osteogenic differentiated autologous adipose-derived stem cells (ASCs), a ceramic material and an extracellular matrix, wherein the biomaterial secretes osteoprotegerin (OPG) and comprises insulin-like growth factor (IGF1) and stromal cell-derived factor 1-alpha (SDF-1α).

In one embodiment, the biomaterial secretes at least about 5 ng of OPG per g of biomaterial. In another embodiment, the biomaterial secretes at least about 10 ng of OPG per g of biomaterial.

In one embodiment, the biomaterial comprises at least about 50 ng of IGF1 per g of biomaterial. In another embodiment, the biomaterial comprises at least about 75 of IGF1 per g of biomaterial.

In one embodiment, the biomaterial comprises at most about 100 ng of SDF-1α per g of biomaterial. In another embodiment, the biomaterial comprises at most about 75 ng of SDF-1α per g of biomaterial.

In one embodiment, the ceramic material is in form of particles. In one embodiment, the ceramic material is particles of calcium phosphate.

In one embodiment, the particles of calcium phosphate have an average size ranging from about 50 μm to about 1500 μm. In one embodiment, the particles of calcium phosphate are particles of hydroxyapatite (HA) and/or β-tricalcium phosphate (β-TCP).

In one embodiment, the particles of calcium phosphate are particles of HA/β-TCP in a ratio ranging from about 10/90 to about 90/10. In another embodiment, the particles of HA/β-TCP are in a ratio from about 20/80 to about 80/20. In another embodiment, the particles of HA/β-TCP are in a ratio from about 30/70 to about 70/30. In another embodiment, the particles of HA/β-TCP are in a ratio from about 40/60 to about 60/40. In another embodiment, the particles of HA/β-TCP are in a ratio of about 50/50. In another embodiment, the particles of HA/β-TCP are in a ratio of 65/35.

In one embodiment, the biomaterial comprises at least about 10 ng of VEGF per g of biomaterial.

In one embodiment, the biomaterial is three-dimensional.

In certain embodiments, the biomaterial is moldable or formable.

The present invention also relates to a medical device or a pharmaceutical composition comprising the multi-dimensional biomaterial of the invention.

Another object of the present invention is a method for producing the multi-dimensional biomaterial of the invention comprising the steps of:
  (a) isolating autologous adipose stem cells (ASCs) from a subject;
  (b) proliferating the ASCs in vitro;
  (c) differentiating the proliferated ASCs; and
  (d) culturing the differentiated ASCs in the presence of a ceramic material.

The present invention further relates to a multi-dimensional biomaterial produced by the method of the invention.

Another object of the present invention is a method for treating a bone or cartilage defect in a subject comprising administering the medical device or pharmaceutical composition of the invention.

In an embodiment, the bone defect is congenital pseudarthrosis of the tibia.

BRIEF DESCRIPTION OF THE DRAWINGS

FIG. 8 is a histogram showing OPG secretion in ng per g of material by ASCs in 2D culture MD medium, and in culture in medium of a biomaterial formed with HA/β-TCP, HA and β-TCP.

FIGS. 9A-9H are a set of graphs showing expression of genes FGFR1 (FIG. 9A), IGFR1 (FIG. 9B), RUNX2 (FIG. 9C), TWIST1 (FIG. 9D), TGFBR1 (FIG. 9E), SMAD2 (FIG. 9F), SMAD4 (FIG. 9G), SMAD5 (FIG. 9H) in the biomaterial of the invention formed with HA/β-TCP (biomaterial) compared to ASCs in MP (MP) and in MD (MD). *: $p<0.05$, : $p<0.01$, *: $p<0.001$.

FIGS. 11A-11B are a set of histograms showing VEGF (FIG. 11A) and SDF-1α (FIG. 11B) secretion in the biomaterial of the invention formed with HA/β-TCP (biomaterial) compared to ASCs in MP (MP) and in MD (MD) in hypoxia (1%) or normoxia (21%).

DETAILED DESCRIPTION

Definitions

Figure 1:
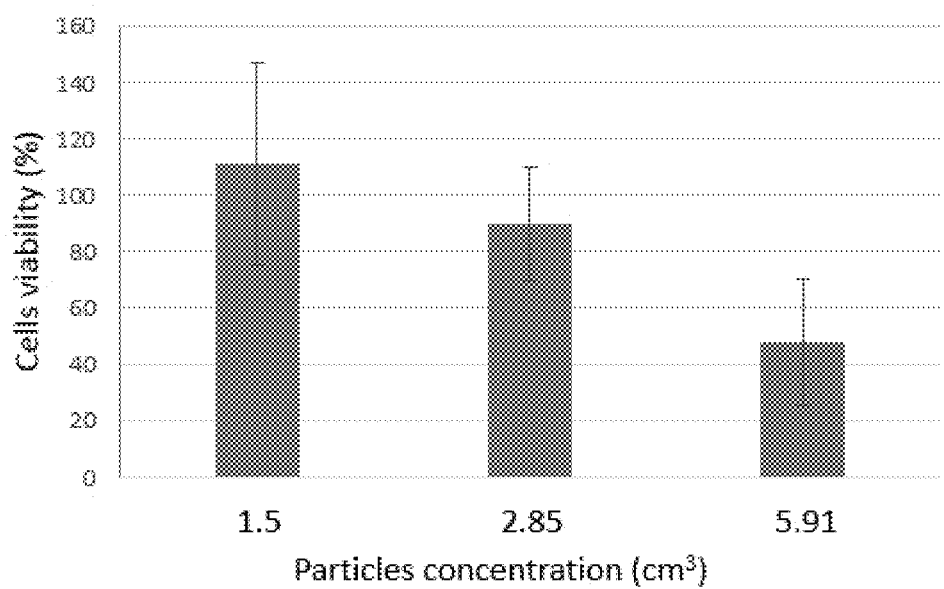
FIG. 1 is a histogram showing cell viability of hASCs in indirect contact with HA/β-TCP at three different concentrations (1.5, 2.85 and 5.91 cm$^3$), in percentage compared to untreated cells.

In the present invention, the following terms have the following meanings:

The term "about" preceding a value means plus or less 10% of the value of said value.

The term "adipose tissue" refers to any fat tissue. The adipose tissue may be brown or white adipose tissue, derived from subcutaneous, omental/visceral, mammary, gonadal, or other adipose tissue site. In particular embodiments, the adipose tissue is subcutaneous white adipose tissue. Such cells may comprise a primary cell culture or an immortalized cell line. The adipose tissue may be from any organism, living or deceased, having fat tissue. In particular embodiments, the adipose tissue is animal, in particular, mammalian, or in particular, the adipose tissue is human. A convenient source of adipose tissue is from liposuction surgery, however, the source of adipose tissue or the method of isolation of adipose tissue is not critical to the invention.

The term "adipose-derived stem cells" (also called "adipose tissue-derived stem cells") as used herein refers to the "non-adipocyte" fraction of adipose tissue. The cells can be fresh, or in culture. "Adipose-derived stem cells" (ASCs) refers to stromal cells that originate from adipose tissue which can serve as precursors to a variety of different cell types such as, but not limited to, adipocytes, osteocytes, and chondrocytes.

The term "ceramic material" as used herein refers to an inorganic, non-metallic, solid material. Ceramic material may be calcium phosphate (CaP), calcium carbonate (CaCO3), calcium sulfate, calcium hydroxide (Ca[OH]2), or combinations thereof. Ceramic material may be in form of particles. Ceramic material may be in form of powder, beads or granules. Ceramic material may be porous.

The term "regeneration" or "tissue regeneration" includes, but is not limited to the growth, generation, or reconstruction of new cells types or tissues from the ASCs of the instant disclosure. In one embodiment, these cells types or tissues include but are not limited to, osteogenic cells (e.g., osteoblasts), chondrocytes, endothelial cells, cardiomyocytes, hematopoietic cells, hepatic cells, adipocytes, neuronal cells, and myotubes. In a particular embodiment, the term "regeneration" or "tissue regeneration" refers to generation or reconstruction of osteogenic cells (e.g. osteoblasts) from the ASCs of the instant disclosure.

The term "growth factors" as used herein are molecules which promote tissue growth, cellular proliferation, vascularization, and the like. In a particular embodiment, the term "growth factors" include molecules which promote bone tissue formation.

The term "cultured" as used herein refers to one or more cells that are undergoing cell division or not undergoing cell division in an in vitro, in vivo, or ex vivo environment. An in vitro environment can be any medium known in the art that is suitable for maintaining cells in vitro, such as suitable liquid media or agar, for example. Specific examples of suitable in vitro environments for cell cultures are described in Culture of Animal Cells: a manual of basic techniques (3rd edition), 1994, R. I. Freshney (ed.), Wiley-Liss, Inc.; Cells: a laboratory manual (vol. 1), 1998, D. L. Spector, R. D. Goldman, L. A. Leinwand (eds.), Cold Spring Harbor Laboratory Press; and Animal Cells: culture and media, 1994, D. C. Darling, S. J. Morgan John Wiley and Sons, Ltd.

The term "confluency" refers to the number of adherent cells in a cell culture surface (such as a culture dish or a flask), i.e., to the proportion of the surface which is covered by cells. A confluency of 100% means the surface is completely covered by the cells. In one embodiment, the expression "cells reach confluence" or "cells are confluent" means that cells cover from 80 to 100% of the surface. In one embodiment, the expression "cells are subconfluent" means that cells cover from 60 to 80% of the surface. In one embodiment, the expression "cells are overconfluent" means that cells covered at least 100% of the surface and/or are 100% confluent since several hours or days.

The term "refrigerating" or "refrigeration" refers to a treatment bringing at temperatures of less than the subject's normal physiological temperature. For example, at one or more temperatures selected in the range of about −196° C. to about +32° C., for extended periods of time, e.g. at least about an hour, at least about a day, at least about a week, at least about 4 weeks, at least about 6 months, etc. In one embodiment, "refrigerating" or "refrigeration" refers to a treatment bringing at temperatures of less than 0° C. The refrigerating may be carried out manually, or in particular, carried out using an ad hoc apparatus capable of executing a refrigerating program. In one embodiment, the term "refrigeration" includes the methods known in the art as "freezing" and "cryopreservation". The skilled person will understand that the refrigerating method may include other steps, including the addition of reagents for that purpose.

The term "non-embryonic cell" as used herein refers to a cell that is not isolated from an embryo. Non-embryonic cells can be differentiated or nondifferentiated. Non-embryonic cells can refer to nearly any somatic cell, such as cells isolated from an ex utero animal. In one embodiment, non-embryonic cells include germinal cells. These examples are not meant to be limiting.

The term "differentiated cell" as used herein refers to a precursor cell that has developed from an unspecialized phenotype to a specialized phenotype. For example, adipose-derived stem cells can differentiate into osteogenic cells.

The term "differentiation medium" as used herein refers to one of a collection of compounds that are used in culture systems of this invention to produce differentiated cells. No limitation is intended as to the mode of action of the compounds. For example, the agent may assist the differentiation process by inducing or assisting a change in phenotype, promoting growth of cells with a particular phenotype or retarding the growth of others. It may also act as an inhibitor to other factors that may be in the medium or synthesized by the cell population that would otherwise direct differentiation down the pathway to an unwanted cell type.

The terms "treatment", "treating" or "alleviation" refers to therapeutic treatments wherein the object is to prevent or slow down (lessen) the bone defect. Those in need of treatment include those already with the disorder as well as those prone to have the disorder or those in whom the bone defect is to be prevented. A subject is successfully "treated" for a bone defect if, after receiving a therapeutic amount of an biomaterial according to the methods of the present invention, the patient shows observable and/or measurable reduction in or absence of one or more of the following: reduction in the bone defect and/or relief to some extent, one or more of the symptoms associated with the bone defect; reduced morbidity and mortality, and improvement in quality of life issues. The above parameters for assessing successful treatment and improvement in the disease are readily measurable by routine procedures familiar to a physician.

In the context of therapeutic use of the disclosed biomaterials, in "allogeneic" therapy, the donor and the recipient are different individuals of the same species, whereas in "autologous" therapy, the donor and the recipient is the same individual, and in "xenogeneic" therapy, the donor derived from an animal of a different species than the recipient.

The term "effective amount" refers to an amount sufficient to effect beneficial or desired results including clinical results. An effective amount can be administered in one or more administrations.

The term "subject" refers to a mammal, in particular, a human. Examples of subjects include humans, non-human primates, dogs, cats, mice, rats, horses, cows and transgenic species thereof. In one embodiment, a subject may be a "patient", i.e., a warm-blooded animal, in particular, a human, who/which is awaiting the receipt of, or is receiving medical care or was/is/will be the object of a medical procedure, or is monitored for the development of a disease. In one embodiment, the subject is an adult (for example a human subject above the age of 18). In another embodiment, the subject is a child (for example a human subject below the age of 18). In one embodiment, the subject is a male. In another embodiment, the subject is a female.

The term "biocompatible" refers to a non-toxic material that is compatible with a biological system such as a cell, cell culture, tissue, or organism.

The term "multi-dimensional" refers to more than one dimension, such as for example two-dimensional (2D) or three-dimensional (3D). In one embodiment, a biomaterial having a multi-dimensional structure refers to a biomaterial having a 2D or 3D structure.

Biomaterials Comprising ASCs

This invention relates to a biomaterial having a multi-dimensional structure comprising adipose tissue-derived stem cells (ASCs), a ceramic material and an extracellular matrix, secreting osteoprotegerin (OPG), and comprising insulin-like growth factor (IGF1) and stromal cell-derived factor 1-alpha (SDF-1α).

In one embodiment, cells are isolated from adipose tissue, and are hereinafter referred to as adipose-derived stem cells (ASCs).

In one embodiment, ASCs tissue is of animal origin, in particular, of mammal origin, or in particular, of human origin. Accordingly, in one embodiment, ASCs are animal ASCs, in particular, mammal ASCs, or in particular, human ASCs. In an exemplary embodiment, ASCs are human ASCs.

Methods of isolating stem cells from adipose tissue are known in the art, and are disclosed for example in Zuk et al. (Tissue Engineering. 2001, 7:211-228). In one embodiment, ASCs are isolated from adipose tissue by liposuction.

As an illustration, adipose tissue may be collected by needle biopsy or liposuction aspiration. ASCs may be isolated from adipose tissue by first washing the tissue sample extensively with phosphate-buffered saline (PBS), optionally containing antibiotics, for example 1% Penicillin/Streptomycin (P/S). Then the sample may be placed in a sterile tissue culture plate with collagenase for tissue digestion (for example, Collagenase Type I prepared in PBS containing 2% P/S), and incubated for 30 min at 37° C., 5% CO2. The collagenase activity may be neutralized by adding culture medium (for example DMEM containing 10% serum). Upon disintegration, the sample may be transferred to a tube. The stromal vascular fraction (SVF), containing the ASCs, is obtained by centrifuging the sample (for example at 2000 rpm for 5 min). To complete the separation of the stromal cells from the primary adipocytes, the sample may be shaken vigorously to thoroughly disrupt the pellet and to mix the cells. The centrifugation step may be repeated. After spinning and the collagenase solution aspirate, the pellet may be resuspended in lysis buffer, incubated on ice (for example for 10 min), washed (for example with PBS/2% P/S) and centrifuged (for example at 2000 rpm for 5 min). The supernatant may be then aspirated, the cell pellet resuspended in medium (for example, stromal medium, i.e. α-MEM, supplemented with 20% FBS, 1% L-glutamine, and 1% P/S), and the cell suspension filtered (for example, through 70 μm cell strainer). The sample containing the cells may be finally plated in culture plates and incubated at 37° C., 5% CO2.

In one embodiment, ASCs of the invention are isolated from the stromal vascular fraction of adipose tissue. In one embodiment, the lipoaspirate may be kept several hours at room temperature, or at +4° C. for 24 hours prior to use, or below 0° C., for example −18° C., for long-term conservation.

In one embodiment, ASCs may be fresh ASCs or refrigerated ASCs. Fresh ASCs are isolated ASCs which have not undergone a refrigerating treatment. Refrigerated ASCs are isolated ASCs which have undergone a refrigerating treatment. In one embodiment, a refrigerating treatment means any treatment below 0° C. In one embodiment, the refrigerating treatment may be performed at about −18° C., at −80° C. or at −180° C. In a specific embodiment, the refrigerating treatment may be cryopreservation.

As an illustration of refrigerating treatment, ASCs may be harvested at 80-90% confluence. After steps of washing and detachment from the dish, cells may be pelleted at room temperature with a refrigerating preservation medium and placed in vials. In one embodiment, the refrigerating preservation medium comprises 80% fetal bovine serum or human serum, 10% dimethylsulfoxide (DMSO) and 10% DMEM/Ham's F-12. Then, vials may be stored at −80° C. overnight. For example, vials may be placed in an alcohol freezing container which cools the vials slowly, at approximately 1° C. every minute, until reaching −80° C. Finally, frozen vials may be transferred to a liquid nitrogen container for long-term storage.

In one embodiment, ASCs are differentiated ASCs. In an exemplary embodiment, ASCs are osteogenic differentiated ACSs. In other words, in an exemplary embodiment, ASCs are differentiated into osteogenic cells. In a particular embodiment, ASCs are differentiated into osteoblasts.

Methods to control and assess the osteogenic differentiation are known in the art. For example, the osteo-differentiation of the cells or tissues of the invention may be assessed by staining of osteocalcin and/or phosphate (e.g. with von Kossa); by staining calcium phosphate (e.g. with Alizarin red); by magnetic resonance imaging (MRI); by measurement of mineralized matrix formation; or by measurement of alkaline phosphatase activity.

In one embodiment, osteogenic differentiation of ASCs is performed by culture of ASCs in osteogenic differentiation medium (MD).

In one embodiment, the osteogenic differentiation medium comprises human serum. In a particular embodiment, the osteogenic differentiation medium comprises human platelet lysate (hPL). In one embodiment, the osteogenic differentiation medium does not comprise any other animal serum. In one embodiment, the osteogenic differentiation medium comprises no other serum than human serum.

In one embodiment, the osteogenic differentiation medium comprises or consists of proliferation medium supplemented with dexamethasone, ascorbic acid and sodium phosphate. In one embodiment, the osteogenic differentiation medium further comprises antibiotics, such as penicillin, streptomycin, gentamycin and/or amphotericin B. In one embodiment, all media are free of animal proteins.

In one embodiment, proliferation medium may be any culture medium designed to support the growth of the cells known to one of ordinary skill in the art. As used herein, the proliferation medium is also called "growth medium". Examples of growth medium include, without limitation, MEM, DMEM, IMDM, RPMI 1640, FGM or FGM-2, 199/109 medium, HamF10/HamF12 or McCoy's 5A. In a particular embodiment, the proliferation medium is DMEM.

In one embodiment, the osteogenic differentiation medium comprises or consists of DMEM supplemented with L-alanyl-L-glutamine (Ala-Gln, also called 'Glutamax®' or 'Ultraglutamine®'), hPL, dexamethasone, ascorbic acid and sodium phosphate. In one embodiment, the osteogenic differentiation medium comprises or consists of DMEM supplemented with L-alanyl-L-glutamine, hPL, dexamethasone, ascorbic and sodium phosphate, and antibiotics, in particular, penicillin, streptomycin, gentamycin and/or amphotericin B.

In one embodiment, the osteogenic differentiation medium comprises or consists of DMEM supplemented with L-alanyl-L-glutamine, hPL (about 5%, v/v), dexamethasone (about 1 ascorbic acid (about 0.25 mM) and sodium phosphate (about 2.93 mM). In one embodiment, the osteogenic differentiation medium comprises or consists of DMEM supplemented with L-alanyl-L-glutamine, hPL (about 5%, v/v), dexamethasone (about 1 ascorbic acid (about 0.25 mM) and sodium phosphate (about 2.93 mM), penicillin (about 100 U/mL) and streptomycin (about 100 µg/mL). In one embodiment, the osteogenic differentiation medium further comprises amphotericin B (about 0.1%).

In one embodiment, the osteogenic differentiation medium consists of DMEM supplemented with L-alanyl-L-glutamine, hPL (about 5%, v/v), dexamethasone (about 1 ascorbic acid (about 0.25 mM) and sodium phosphate (about 2.93 mM). In one embodiment, the osteogenic differentiation medium comprises or consists of DMEM supplemented with L-alanyl-L-glutamine, hPL (about 5%, v/v), dexamethasone (about 1 µM), ascorbic acid (about 0.25 mM) and sodium phosphate (about 2.93 mM), penicillin (about 100 U/mL), streptomycin (about 100 µg/mL) and amphotericin B (about 0.1%).

In one embodiment, the ASCs are late passaged adipose-derived stem cells. As used herein, the term "late passages" means adipose-derived stem cells differentiated at least after passage 4. As used herein, the passage 4 refers to the fourth passage, i.e. the fourth act of splitting cells by detaching them from the surface of the culture vessel before they are resuspended in fresh medium. In one embodiment, late passaged adipose-derived stem cells are differentiated after passage 4, passage 5, passage 6 or more. In a particular embodiment, ASCs are differentiated after passage 4.

As used herein, the term "vessel" means any cell culture surface, such as for example a flask or a well-plate.

The initial passage of the primary cells was referred to as passage 0 (P0). According to the present invention, passage P0 refers to the seeding of cell suspension from the pelleted Stromal Vascular Fraction (SVF) on culture vessels. Therefore, passage P4 means that cells were detached 4 times (at P1, P2, P3 and P4) from the surface of the culture vessel (for example by digestion with trypsin) and resuspended in fresh medium.

In one embodiment, the ASCs of the invention are cultured in proliferation medium up to the fourth passage. In one embodiment, the ASCs of the invention are cultured in differentiation medium after the fourth passage. Accordingly, in one embodiment, at passages P1, P2 and P3, ASCs are detached from the surface of the culture vessel and then diluted to the appropriate cell density in proliferation medium. Still according to this embodiment, at passage P4, ASCs are detached from the surface of the culture vessel and then diluted to the appropriate cell density in differentiation medium. Therefore, according to this embodiment, at P4 the ASCs of the invention are not resuspended and cultured in proliferation medium until they reach confluence before being differentiated (i.e. before being cultured in differentiation medium), but are directly resuspended and cultured in differentiation medium.

In one embodiment, cells are maintained in osteogenic differentiation medium at least until they reach confluence, in particular, between 70% and 100% confluence, or between between 80% and 95% confluence. In one embodiment, cells are maintained in osteogenic differentiation medium for at least 5 days, in particular, at least 10 days, or at least 15 days. In one embodiment, cells are maintained in osteogenic differentiation medium from 5 to 30 days, in particular, from 10 to 25 days, or from 15 to 20 days. In one embodiment, differentiation medium is replaced every 2 days. However, as it is known in the art, the cell growth rate from one donor to another could slightly differ. Thus, the duration of the osteogenic differentiation and the number of medium changes may vary from one donor to another.

In one embodiment, cells are maintained in osteogenic differentiation medium at least until formation of osteoid, i.e. the unmineralized, organic portion of the bone matrix that forms prior to the maturation of bone tissue.

In one embodiment, the ceramic material of the invention is in form of particles, herein referred to as ceramic particles. In one embodiment, particles may be beads, powder, spheres, microspheres, and the like.

In one embodiment, the ceramic material of the invention are particles of calcium phosphate (CaP), calcium carbonate (CaCO3), calcium sulfate, or calcium hydroxide (Ca[OH]2), or combinations thereof.

Examples of calcium phosphate particles include, but are not limited to, hydroxyapatite (HA, $Ca_{10}(PO_4)_6(OH)_2$), tricalcium phosphate (TCP, $Ca_3[PO_4]_2$), α-tricalcium phosphate (α-TCP, $α-Ca_3(PO_4)_2$), β-tricalcium phosphate (β-TCP, $β-Ca_3(PO_4)_2$), tetracalcium phosphate (TTCP, $Ca_4(PO_4)_2O$), octacalcium phosphate ($Ca_8H_2(PO_4)_{6.5}H_2O$), amorphous calcium phosphate ($Ca_3(PO_4)_2$), hydroxyapatite/β-tricalcium phosphate (HA/β-TCP), hydroxyapatite/tetracalcium phosphate (HA/TTCP), and the like.

In one embodiment, the ceramic material of the invention comprises or consists of hydroxyapatite (HA), tricalcium phosphate (TCP), hydroxyapatite/β-tricalcium phosphate (HA/β-TCP), calcium sulfate, or combinations thereof. In one embodiment, the ceramic material of the invention comprises or consists of hydroxyapatite (HA), β-tricalcium phosphate (β-TCP), hydroxyapatite/β-tricalcium phosphate (HA/β-TCP), α-tricalcium phosphate (α-TCP), calcium sulfate, or combinations thereof.

In one embodiment, the ceramic particles of the invention are particles of hydroxyapatite (HA). In another embodiment, the ceramic particles of the invention are particles of β-tricalcium phosphate (β-TCP). In another embodiment, the ceramic particles of the invention are particles of hydroxyapatite/β-tricalcium phosphate (HA/β-TCP). In other words, in one embodiment, the ceramic particles of the invention are a mixture of hydroxyapatite and β-tricalcium phosphate particles (called HA/β-TCP particles). In one embodiment, the ceramic particles of the invention consist of hydroxyapatite particles and β-tricalcium phosphate particles (called HA/β-TCP particles).

In one embodiment, the ceramic particles, in particular, HA, β-TCP and/or HA/β-TCP particles, are in form of granules, powder or beads. In one embodiment, the ceramic particles, in particular, HA, β-TCP and/or HA/β-TCP particles, are in form of porous granules, powder or beads. In one embodiment, the ceramic particles, in particular, HA, β-TCP and/or HA/β-TCP particles, are porous ceramic material. In one embodiment, the ceramic particles, in particular, HA, β-TCP and/or HA/β-TCP particles, are powder particles. In a particular embodiment, the ceramic particles, in particular, HA, β-TCP and/or HA/β-TCP particles, are in form of porous granules. In another particular embodiment, the ceramic particles, in particular, HA, β-TCP and/or HA/β-TCP particles, are in form of powder. In one embodiment, the ceramic particles, in particular, HA, β-TCP and/or HA/β-TCP particles, are not structured to form a predefined 3D shape or scaffold, such as for example a cube. In one embodiment, the ceramic material of the invention is not a 3D scaffold. In one embodiment, the ceramic material has not a predefined shape or scaffold. In one embodiment, the ceramic material of the invention has not the form of a cube. In one embodiment, the biomaterial of the invention is scaffold-free.

In one embodiment, the ceramic particles of the invention, preferably HA, β-TCP and/or HA/β-TCP particles, are larger than about 50 μm, in particular, larger than about 100 μm. In one embodiment, the ceramic particles of the invention, in particular, HA, β-TCP and/or HA/β-TCP particles, have a mean diameter larger than about 50 μm, in particular, larger than about 100 μm.

In one embodiment, the ceramic particles of the invention, in particular, HA, β-TCP and/or HA/β-TCP particles, have a mean diameter of at least about 50 μm, in particular, of at least about 100 μm, or of at least about 150 μm. In another embodiment, the ceramic particles of the invention, in particular, HA, β-TCP and/or HA/β-TCP particles, have a mean diameter of at least about 200 μm, in particular, of at least about 250 μm, or of at least about 300 μm.

In another embodiment, the ceramic particles of the invention, in particular, HA, β-TCP and/or HA/β-TCP particles, have a mean diameter of at most about 2500 μm, in particular, of at most about 2000 μm, or of at least most about 1500 μm. In one embodiment, the ceramic particles of the invention, in particular, HA, β-TCP and/or HA/β-TCP particles, have a mean diameter of at most about 1000 μm, 900 μm, 800 μm, 700 μm or 600 μm.

In one embodiment, the ceramic particles of the invention, in particular, HA, β-TCP and/or HA/β-TCP particles, have a mean diameter ranging from about 50 μm to about 1500 μm, in particular, from about 50 μm to about 1250 μm, or from about 100 μm to about 1000 μm. In one embodiment, the ceramic particles of the invention, in particular, HA, β-TCP and/or HA/β-TCP particles, have a mean diameter ranging from about 100 μm to about 800 μm, in particular, from about 150 μm to about 700 μm, or from about 200 μm to about 600 μm.

In one embodiment, the HA/β-TCP particles have a mean diameter ranging from about 50 μm to about 1500 μm, in particular, from about 50 μm to about 1250 μm, or from about 100 μm to about 1000 μm. In one embodiment, the HA and β-TCP particles have a mean diameter ranging from about 100 μm to about 800 μm, in particular, from about 150 μm to about 700 μm, or from about 200 μm to about 600 μm.

In one embodiment, the ratio between HA and β-TCP (HA/β-TCP ratio) in the particles ranges from about 0/100 to about 100/0, in particular, from about 10/90 to about 90/10, or from about 20/80 to about 80/20. In one embodiment, the ratio HA/β-TCP in the particles ranges from about 30/70 to about 70/30, from about 35/65 to about 65/35, or from about 40/60 to about 60/40.

In one embodiment, the HA/β-TCP ratio in the particles is 0/100, i.e. the particles are particles of β-tricalcium phosphate. In another embodiment, the HA/β-TCP ratio in the particles is 100/0, i.e. the particles are particles of hydroxyapatite. In one embodiment, the HA/β-TCP ratio in the particles is about 10/90. In another embodiment, the HA/β-TCP ratio in the particles is about 90/10. In one embodiment, the HA/β-TCP ratio in the particles is about 20/80. In another embodiment, the HA/β-TCP ratio in the particles is about 80/20. In one embodiment, the HA/β-TCP ratio in the particles is about 30/70. In another embodiment, the HA/β-TCP ratio in the particles is about 70/30. In another embodiment, the HA/β-TCP ratio in the particles is 35/65. In another embodiment, the HA/β-TCP ratio in the particles is 65/35. In one embodiment, the HA/β-TCP ratio in the particles is about 40/60. In another embodiment, the HA/β-TCP ratio in the particles is about 60/40. In another embodiment, the HA/β-TCP ratio in the particles is 50/50.

In one embodiment, the HA/β-TCP ratio in the particles is 100 to 0, 99 to 1, 98 to 2, 97 to 3, 96 to 4, 95 to 5, 94 to 6, 93 to 7, 92 to 8, 91 to 9, 90 to 10, 89 to 11, 88 to 12, 87 to 13, 86 to 14, 85 to 15, 84 to 16, 83 to 17, 82 to 18, 81 to 19, 80 to 20, 79 to 21, 78 to 22, 77 to 23, 76 to 24, 75 to 25, 74 to 26, 73 to 27, 72 to 28, 71 to 29, 70 to 30, 69 to 31, 68 to 32, 67 to 33, 66 to 34, 65 to 35, 64 to 36, 63 to 37, 62 to 38, 61 to 39, 60 to 40, 59 to 41, 58 to 42, 57 to 43, 56 to 44, 55 to 45, 54 to 46, 53 to 47, 52 to 48, 51 to 49, 50 to 50, 49 to 51, 48 to 52, 47 to 53, 46 to 54, 45 to 55, 44 to 56, 43 to 57, 42 to 58, 41 to 59, 40 to 60, 39 to 61, 38 to 62, 37 to 63, 36 to 64, 35 to 65, 34 to 66, 33 to 67, 32 to 68, 31 to 69, 30 to 70, 29 to 71, 28 to 72, 27 to 73, 26 to 74, 25 to 75, 24 to 76, 23 to 77, 22 to 78, 21 to 79, 20 to 80, 19 to 81, 18 to 82, 17 to 83, 16 to 84, 15 to 85, 14 to 86, 13 to 87, 12 to 88, 11 to 89, 10 to 90, 9 to 91, 8 to 92, 7 to 93, 6 to 94, 5 to 95, 4 to 96, 3 to 97, 2 to 98, 1 to 99, or 0 to 100.

According to one embodiment, the quantity of ceramic particles, in particular, HA, β-TCP and/or HA/β-TCP, is optimal for providing a 3D structure to the biomaterial. In one embodiment, the ceramic particles, in particular, HA, β-TCP and/or HA/β-TCP particles, are added at a concentration ranging from about 0.1 cm$^3$ to about 5 cm$^3$ for a 150 cm$^2$ vessel, in particular, from about 0.5 cm$^3$ to about 3 cm$^3$, or from about 1 cm$^3$ to about 2 cm$^3$. In a particular embodiment, the ceramic particles, in particular, HA, β-TCP and/or HA/β-TCP particles, are added at a concentration of about 1.5 cm$^3$ for a 150 cm$^2$ vessel.

In one embodiment, the ceramic particles, in particular, HA, TCP and/or HA/β-TCP particles, are added at a concentration ranging from about $7.10^{-3}$ to $7.10^{-2}$ cm$^3$ per mL of medium. In one embodiment, the ceramic particles, in particular, HA, TCP and/or HA/β-TCP particles, are added at a concentration ranging from about $3.3.10^{-3}$ to $3.3.10^{-2}$ cm$^3$ per cm$^2$ of vessel.

In one embodiment, the ceramic material of the invention is added after differentiation. In one embodiment, the material of the invention is added when cells are subconfluent. In one embodiment, the biocompatible, e.g., ceramic material of the invention is added when cells are overconfluent. In one embodiment, ceramic material of the invention is added when cells have reached confluence after differentiation. In others words, in one embodiment, ceramic material of the invention are added when cells have reached confluence in differentiation medium. In one embodiment, ceramic material of the invention are added at least 5 days after P4, in particular, 10 days, or in particular, 15 days. In one embodiment, ceramic material of the invention are added from 5 to 30 days after P4, in particular, from 10 to 25 days, or in particular, from 15 to 20 days.

In one embodiment, the biomaterial according to the invention is two-dimensional. In this embodiment, the biomaterial of the invention may form a thin film of less than 1 mm.

In another embodiment, the biomaterial according to the invention is three-dimensional. In this embodiment, the biomaterial of the invention may form a thick film having a thickness of at least 1 mm. The size of the biomaterial may be adapted to the use.

In one embodiment, the biomaterial of the invention does not comprise a scaffold. As used herein, the term "scaffold" means a structure that mimics the porosity, pore size, and/or function of native mammal tissues, including human tissues, such as native mammal bones or extracellular matrix. Examples of such scaffolds include, but are not limited to, artificial bone, collagen sponges, hydrogels, such as protein hydrogels, peptide hydrogels, polymer hydrogels and wood-based nanocellulose hydrogels, and the like. In one embodiment, the biomaterial of the invention does not comprise an artificial bone. In one embodiment, the ceramic material of the invention is not an artificial bone.

In one embodiment, the multi-dimension of the biomaterial of the invention is not due to a scaffold mimicking natural extracellular matrix structure. In one embodiment, the biomaterial of the invention does not comprise a scaffold mimicking natural extracellular matrix structure.

In one embodiment, the multi-dimension of the biomaterial of the invention is due to the synthesis of extracellular matrix by adipose tissue-derived stem cells of the invention.

In one embodiment, the biomaterial of the invention comprises an extracellular matrix. In one embodiment, the extracellular matrix of the invention derives from the ASCs. In one embodiment, the extracellular matrix of the invention is produced by the ASCs.

As used herein, the term "extracellular matrix" (ECM) means a non-cellular three-dimensional macromolecular network. Matrix components of ECM bind each other as well as cell adhesion receptors, thereby forming a complex network into which cells reside in tissues or in biomaterials of the invention.

In one embodiment, the extracellular matrix of the invention comprises collagen, proteoglycans/glycosaminoglycans, elastin, fibronectin, laminin, and/or other glycoproteins. In a particular embodiment, the extracellular matrix of the invention comprises collagen. In another particular embodiment, the extracellular matrix of the invention comprises proteoglycans. In another particular embodiment, the extracellular matrix of the invention comprises collagen and proteoglycans. In one embodiment, the extracellular matrix of the invention comprises growth factors, proteoglycans, secreting factors, extracellular matrix regulators, and glycoproteins.

In one embodiment, the ASCs within the biomaterial of the invention form a tissue, herein referred to as ASCs tissue. In one embodiment, the ASCs and the ceramic material, in particular, the ceramic particles, or in particular, HA, β-TCP and/or HA/β-TCP particles, within the biomaterial of the invention are embedded in the extracellular matrix. In one embodiment, the ASCs, in particular, differentiated in osseous cells, with the ceramic material, in particular, the ceramic particles, or in particular, HA, β-TCP and/or HA/β-TCP particles, form a 3D structure with the extracellular matrix. In one embodiment, the ASCs tissue is a vascularized tissue. In one embodiment, the biomaterial of the invention is vascularized.

In one embodiment, the ASCs tissue is a cellularized interconnective tissue. In one embodiment, the ceramic particles are integrated in the cellularized interconnective tissue. In one embodiment, the ceramic particles are dispersed within the ASCs tissue.

In one embodiment, the biomaterial of the invention is characterized by an interconnective tissue formed between ceramic particles. In one embodiment, the biomaterial of the invention is characterized by mineralization surrounding ceramic particles. In one embodiment, the tissular nature of the formed biomaterial may be confirmed by the occurrence of a tissular retraction.

In one embodiment, the biomaterial of the invention has the same properties as a real bone with osteocalcin expression and mineralization properties. In one embodiment, the biomaterial of the invention comprises osseous cells. In one embodiment, the biomaterial of the invention comprises osseous cells and an extracellular matrix. In one embodiment, the biomaterial of the invention comprises osseous cells and collagen. In a particular embodiment, the collagen is calcified and mineralized collagen. In one embodiment, the biomaterial of the invention comprises an osseous matrix.

In one embodiment, the biomaterial of the invention is such that the differentiation of the cells of the biomaterial has reached an end point, and the phenotype of the biomaterial will remain unchanged when implanted.

In one embodiment, the biomaterial of the invention comprises growth factors. In one embodiment, the growth factors content or secretion by the biomaterial of the invention is assessed at 4, 5, 6, 7 or 8 weeks after addition of the biocompatible material.

Osteoprotegerin (OPG), also known as osteoclastogenesis inhibitory factor (OCIF), or tumor necrosis factor receptor superfamily member 11B (TNFRSF11B), is a cytokine receptor. It was found that overexpression or administration of OPG blunts osteoclastogenesis in mice. Similarly, it was established that animals lacking OPG have accelerated osteoclastogenesis and develop severe osteoporosis. OPG is now known to be a soluble decoy receptor that competes with RANK for RANKL (Receptor Activator of Nuclear factor Kappa-B Ligand, also known as tumor necrosis factor ligand superfamily member 11 (TNFSF11), TNF-related activation-induced cytokine (TRANCE), osteoprotegerin ligand (OPGL), or osteoclast differentiation factor (ODF)). RANK/RANKL/OPG signaling pathway has been identified as regulating osteoclast differentiation and activation. Therefore, the balance between the expression of the stimulator of osteoclastogenesis, RANKL, and of the inhibitor, OPG, dictates the quantity of bone resorbed.

In one embodiment, the OPG content and/or secretion of the biomaterial of the invention may be quantified by any method known in the art, such as for example by ELISA, in particular, at 4, 5, 6, 7, or 8 weeks after addition of the biocompatible material.

In one embodiment, the biomaterial of the invention comprises OPG. In one embodiment, the biomaterial of the invention secretes OPG. In one embodiment, the ASCs of the biomaterial of the invention secrete OPG. In one embodiment, cell-engineered biomaterial of the invention secretes OPG.

In one embodiment, the biomaterial of the invention secretes at least about 1000, 1250, 1500, 1750 or 2000 pg of OPG per $10^6$ cells. In one embodiment, the biomaterial of the invention secretes at least about 2100, 2200, 2300, 2400 or 2500 pg of OPG per $10^6$ cells. In another embodiment, the biomaterial of the invention secretes at least about 2550, 2600, 2650 or 2700 pg of OPG per $10^6$ cells. In another embodiment, the biomaterial of the invention secretes at least about 2750, 2800, 2850, 2900 or 2950 pg of OPG per $10^6$ cells.

In one embodiment, the biomaterial of the invention secretes at least about 2750 pg of OPG per $10^6$ cells. In another embodiment, the biomaterial of the invention secretes about 2500 pg of OPG per $10^6$ cells. In another embodiment, the biomaterial of the invention secretes about 3000 pg of OPG per $10^6$ cells.

In one embodiment, the biomaterial of the invention secretes from about 1000 to about 10000 pg of OPG per $10^6$ cells, in particular, from about 1250 to about 7500 pg/$10^6$ cells, or in particular, from about 1500 to about 5000 pg/$10^6$ cells. In one embodiment, the biomaterial of the invention secretes from about 1000 to about 5000 pg of OPG per $10^6$ cells, in particular, from about 1250 to about 4500 pg/$10^6$ cells, or in particular, from about 1500 to about 4000 pg/$10^6$ cells. In a preferred embodiment, the biomaterial of the invention secretes OPG at a concentration ranging from about 2000 to about 3500 pg/$10^6$ cells. In a particular embodiment, the biomaterial of the invention secretes OPG at a concentration of about 3000 or 3500 pg/$10^6$ cells.

In one embodiment, the biomaterial of the invention secretes at least about 5 ng of OPG per g of biomaterial, in particular, at least about 10 ng/g, or in particular, at least about 15 ng/g. In another embodiment, the biomaterial of the invention secretes at least about 20 ng of OPG per g of biomaterial, in particular, at least about 25 ng/g, or in particular, at least about 30 ng/g.

In another embodiment, the biomaterial of the invention secretes at least about 50 ng of OPG per g of biomaterial, in particular, at least about 60 ng/g, or in particular, at least about 70 ng/g. In one embodiment, the biomaterial of the invention secretes at least about 75 ng of OPG per g of biomaterial. In another embodiment, the biomaterial of the invention secretes at least about 80 ng of OPG per g of biomaterial.

In one embodiment, the biomaterial of the invention secretes from about 5 to about 200 ng of OPG per gram of biomaterial, in particular, from about 10 to about 175 ng/g, or in particular, from about 15 to about 150 ng/g. In another embodiment, the biomaterial of the invention secretes from about 10 to about 200 ng of OPG per gram of biomaterial, in particular, from about 15 to about 175 ng/g, or in particular, from about 20 to about 150 ng/g, or in particular, from about 25 to about 125 ng/g. In one embodiment, the biomaterial of the invention secretes from about 20 to about 100 ng/g of biomaterial. In another embodiment, the biomaterial of the invention secretes from about 25 to about 100 ng/g of biomaterial. In another embodiment, the biomaterial of the invention secretes from about 30 to about 100 ng/g of biomaterial, from about 30 to about 90 ng/g of biomaterial or from about 30 to about 85 ng/g of biomaterial.

In one particular embodiment, the biomaterial of the invention secretes OPG at a concentration of about 30 ng/g of biomaterial. In another particular embodiment, the biomaterial of the invention secretes OPG at a concentration of about 75 ng/g of biomaterial. In another particular embodiment, the biomaterial of the invention secretes OPG at a concentration of about 85 ng/g of biomaterial.

In one embodiment, the biomaterial of the invention secretes OPG at concentrations as described herein above after 4, 5, 6, 7 or 8 weeks after addition of the ceramic material. In other words, in one embodiment, the biomaterial of the invention secretes OPG at concentrations as described herein above after 4, 5, 6, 7 or 8 weeks after the beginning of the multi-dimensional induction.

In one embodiment, the RANKL content and/or secretion of the biomaterial of the invention may be quantified by any method known in the art, such as for example by ELISA, in particular, at 4, 5, 6, 7, or 8 weeks after addition of the ceramic material.

In one embodiment, the level of RANKL in the biomaterial of the invention or in supernatants of the biomaterial when in a medium is undetectable. In one embodiment, the level of RANKL is expressed in pg per mL of supernatant. In one embodiment, the biomaterial of the invention comprises or the ASCs of the biomaterial secrete less than 200 pg of RANKL per mL, in particular, less than 156 pg/mL, in particular, less than 100 pg/mL, or in particular, less than 78 pg/mL, or in particular, less than 50 pg/mL, or in particular, less than 10 pg/mL, or in particular, less than 7.8 pg/mL.

In one embodiment, the biomaterial of the invention does not substantially comprise RANKL. In one embodiment, the ASCs of the biomaterial of the invention do not substantially secrete RANKL.

In one embodiment, the biomaterial of the invention secretes RANKL at concentrations as described herein above after 4, 5, 6, 7 or 8 weeks after addition of the ceramic material. In other words, in one embodiment, the biomaterial of the invention secretes RANKL at concentrations as described herein above after 4, 5, 6, 7 or 8 weeks after the beginning of the multi-dimensional induction.

In one embodiment, the biomaterial of the invention secretes OPG and does not secrete RANKL, or does not secrete detectable levels of RANKL.

In one embodiment, the biomaterial of the invention secretes OPG in a concentration of at least as described hereinabove, and secretes RANKL in a concentration of at most as described hereinabove.

In one embodiment, the biomaterial of the invention displays a bone resorption inhibition activity. In one embodiment, the bone resorption inhibition activity includes the secretion of osteoprotegerin (OPG). In one embodiment, the bone resorption inhibition activity includes the secretion of OPG and the low or no secretion of RANKL.

Insulin-like growth factor (IGF-1) is positively associated with maintenance of bone mineral density and acquisition of a higher peak bone mass which reduces subsequent fracture risk.

In one embodiment, the IGF-1 content of the biomaterial of the invention may be quantified by any method known in the art, such as for example by ELISA, in particular, at 4, 5, 6, 7, or 8 weeks after addition of the ceramic material.

In one embodiment, the biomaterial of the invention comprises IGF-1. In a particular embodiment, the biomaterial of the invention comprises high levels of IGF-1.

In one embodiment, the biomaterial of the invention comprises IGF-1 at a concentration of at least about 50 ng/g of biomaterial, in particular, at least about 60 ng/g, or in particular, at least about 70 ng/g, or in particular, at least about 80 ng/g. In one embodiment, the biomaterial of the invention comprises IGF-1 at a concentration of at least about 90, 91, 92, 93, 94, 95, 96, 97, 98, 99 or 100 ng/g of biomaterial.

In one embodiment, the biomaterial of the invention comprises IGF-1 at a concentration ranging from about 10 ng/g to about 500 ng/g of biomaterial, in particular, from about 20 ng/g to about 400 ng/g, or in particular, from about 30 ng/g to about 300 ng/g, or in particular, from about 40 ng/g to about 250 ng/g.

In one embodiment, the biomaterial of the invention comprises IGF-1 at a concentration ranging from about 50 ng/g to about 200 ng/g of biomaterial, in particular, from about 60 ng/g to about 175 ng/g, or in particular, from about 70 ng/g to about 150 ng/g. In one embodiment, the biomaterial of the invention comprises IGF-1 at a concentration ranging from about 80 ng/g to about 150 ng/g of biomaterial, in particular, from about 85 ng/g to about 125 ng/g, or in particular, from about 90 ng/g to about 100 ng/g.

In one embodiment, the biomaterial of the invention comprises IGF-1 at a concentration ranging from about 90 ng/g to about 500 ng/g of biomaterial, from about 90 ng/g to about 400 ng/g, from about 90 ng/g to about 300 ng/g, from about 90 ng/g to about 200 ng/g, from about 90 ng/g to about 150 ng/g, from about 90 ng/g to about 125 ng/g or from about 90 ng/g to about 100 ng/g.

In one embodiment, the biomaterial of the invention comprises IGF-1 at a concentration of about 90, 91, 92, 93, 94, 95, 96, 97, 98, 99 or 100 ng/g of biomaterial. In one embodiment, the biomaterial of the invention comprises about 90 ng of IGF-1 per gram of biomaterial. In another embodiment, the biomaterial of the invention comprises about 95 ng of IGF-1 per gram of biomaterial. In another embodiment, the biomaterial of the invention comprises about 100 ng of IGF-1 per gram of biomaterial.

In one embodiment, the biomaterial of the invention comprises IGF-1 at concentrations as described herein above after 4, 5, 6, 7 or 8 weeks after addition of the ceramic material. In other words, in one embodiment, the biomaterial of the invention comprises IGF-1 at concentrations as described herein above after 4, 5, 6, 7 or 8 weeks after the beginning of the multi-dimensional induction.

SDF-1α, also called stromal cell-derived factor 1-alpha or CXCL12, plays a stimulatory role in osteoclast differentiation and activation. Osteoclasts, and especially osteoclast precursors, are highly positive for CXCR4, a unique receptor for SDF-1α. Although SDF-1α induces osteoclastogenesis directly, it was recently found that SDF-1α can indirectly impact osteoclastogenesis via up-regulation of RANKL expression. The presence of RANK on osteoclasts and their precursors suggested that osteoclast-differentiating factor, residing on stromal cells, may be RANKL.

In one embodiment, the SDF-1α content of the biomaterial of the invention may be quantified by any method known in the art, such as for example by ELISA, in particular, at 4, 5, 6, 7, or 8 weeks after addition of the ceramic material.

In one embodiment, the biomaterial of the invention comprises SDF-1α. In a particular embodiment, the biomaterial of the invention comprises low levels of SDF-1α.

In one embodiment, the biomaterial of the invention comprises SDF-1α at a concentration of at most about 300 ng/g of biomaterial, in particular, at most about 250 ng/g, or in particular, at most about 200 ng/g, even more preferably at most about 150 ng/g. In one embodiment, the biomaterial of the invention comprises SDF-1α at a concentration of at most about 100 ng/g of biomaterial, in particular, at most about 90 ng/g, or in particular, at most about 80 ng/g. In one embodiment, the biomaterial of the invention comprises SDF-1α at a concentration of at most about 75 ng/g of biomaterial, about 70 ng/g, about 65 ng/g, about 60 ng/g or about 55 ng/g. In one embodiment, the biomaterial of the invention comprises SDF-1α at a concentration of at most about 59, 58, 57, 56, 55, 54, 53, 52 or 51 ng/g of biomaterial.

In one embodiment, the biomaterial of the invention comprises SDF-1α at a concentration of at most about 50 ng/g of biomaterial. In one embodiment, the biomaterial of the invention comprises SDF-1α at a concentration of at most about 49, 48, 47, 46, 45, 44, 43, 42 or 41 ng/g of biomaterial. In a particular embodiment, the biomaterial of the invention comprises SDF-1α at a concentration of at most about 40 ng/g of biomaterial. In one embodiment, the biomaterial of the invention comprises SDF-1α at a concentration of at most about 39, 38, 37, 36, 35, 34, 33, 32 or 31 ng/g of biomaterial. In a particular embodiment, the biomaterial of the invention comprises SDF-1α at a concentration of at most about 30 ng/g of biomaterial.

In one embodiment, the biomaterial of the invention comprises SDF-1α at a concentration ranging from about 5 ng/g to about 100 ng/g of biomaterial, in particular, from about 10 ng/g to about 90 ng/g, or in particular, from about 15 ng/g to about 90 ng/g. In another embodiment, the biomaterial of the invention comprises SDF-1α at a concentration ranging from about 20 ng/g to about 80 ng/g of biomaterial, in particular, from about 25 ng/g to about 70 ng/g, or in particular, from about 25 ng/g to about 60 ng/g. In one embodiment, the biomaterial of the invention comprises SDF-1α at a concentration ranging from about 25 ng/g to about 55 ng/g of biomaterial. In one embodiment, the biomaterial of the invention comprises SDF-1α at a concentration ranging from about 30 ng/g to about 100 ng/g of biomaterial, from about 30 ng/g to about 90 ng/g, from about 30 ng/g to about 80 ng/g, from about 30 ng/g to about 70 ng/g, from about 30 ng/g to about 60 ng/g, from about 30 ng/g to about 55 ng/g, or from about 30 ng/g to about 50 ng/g.

In one embodiment, the biomaterial of the invention comprises about 30 ng of SDF-1α per gram of biomaterial. In another embodiment, the biomaterial of the invention comprises about 40 ng of SDF-1α per gram of biomaterial. In another embodiment, the biomaterial of the invention comprises about 50 ng of SDF-1α per gram of biomaterial.

In one embodiment, the biomaterial of the invention comprises SDF-1α at concentrations as described herein above after 4, 5, 6, 7 or 8 weeks after addition of the ceramic material. In other words, in one embodiment, the biomaterial of the invention comprises SDF-1α at concentrations as described herein above after 4, 5, 6, 7 or 8 weeks after the beginning of the multi-dimensional induction.

In one embodiment, the biomaterial of the invention secretes OPG at concentrations as described herein above, comprises IGF1 at concentrations as described hereinabove and comprises SDF-1α at concentrations as described herein above.

In a particular embodiment, the biomaterial of the invention:
  secretes at least about 5 ng of OPG per g of biomaterial, in particular, at least about 10 ng/g, or in particular, at least about 15 ng/g,
  comprises at least about 10 ng of IGF1 per g of biomaterial, in particular, at least about 25 ng/g, or in particular, at least about 50 ng/g, and
  comprises at most about 200 ng of SDF-1α per g of biomaterial, in particular, at most about 150 ng/g, or in particular, at most about 100 ng/g.

In another particular embodiment, the biomaterial of the invention:
  secretes at least about 10 ng of OPG per g of biomaterial, in particular, at least about 20 ng/g, or in particular, at least about 30 ng/g, comprises at least about 50 ng of IGF1 per g of biomaterial, in particular, at least about 75 ng/g, or in particular, at least about 90 ng/g, and comprises at most about 100 ng of SDF-1α per g of biomaterial, in particular, at most about 75 ng/g, or in particular, at most about 50 ng/g.

In one embodiment, the biomaterial of the invention comprises vascular endothelial growth factor (VEGF). In a particular embodiment, the biomaterial of the invention comprises high levels of VEGF.

In one embodiment, the VEGF content of the biomaterial of the invention may be quantified by any method known in the art, such as for example by ELISA, in particular, at 4, 5, 6, 7, or 8 weeks after addition of the ceramic material.

In one embodiment, the biomaterial of the invention comprises VEGF at a concentration of at least about 10 ng/g of biomaterial, in particular, at least about 20 ng/g, or in particular, at least about 30 ng/g. In another embodiment, the biomaterial of the invention comprises VEGF at a concentration of at least about 50 ng/g of biomaterial, about 60 ng/g, about 70 ng/g, or about 75 ng/g. In another embodiment, the biomaterial of the invention comprises VEGF at a concentration of at least about 95 or 100 ng/g of biomaterial.

In one embodiment, the biomaterial of the invention comprises VEGF at a concentration ranging from about 10 ng/g to about 150 ng/g of biomaterial, in particular, from about 20 ng/g to about 125 ng/g, or in particular, from about 25 ng/g to about 100 ng/g. In another embodiment, the biomaterial of the invention comprises VEGF at a concentration ranging from about 20 ng/g to about 100 ng/g of biomaterial. In another embodiment, the biomaterial of the invention comprises VEGF at a concentration ranging from about 30 ng/g to about 100 ng/g of biomaterial. In another embodiment, the biomaterial of the invention comprises VEGF at a concentration ranging from about 35 ng/g to about 100 ng/g of biomaterial. In another embodiment, the biomaterial of the invention comprises VEGF at a concentration ranging from about 35 ng/g to about 95 ng/g of biomaterial.

In one embodiment, the biomaterial of the invention comprises VEGF at a concentration of about 35 ng/g of biomaterial. In another embodiment, the biomaterial of the invention comprises VEGF at a concentration of about 75 ng/g of biomaterial. In another embodiment, the biomaterial of the invention comprises VEGF at a concentration of about 95 ng/g of biomaterial. In another embodiment, the biomaterial of the invention comprises VEGF at a concentration of about 100 ng/g of biomaterial.

In one embodiment, the biomaterial of the invention comprises VEGF at concentrations as described herein above after 4, 5, 6, 7 or 8 weeks after addition of the ceramic material. In other words, in one embodiment, the biomaterial of the invention comprises VEGF at concentrations as described herein above after 4, 5, 6, 7 or 8 weeks after the beginning of the multi-dimensional induction.

Bone morphogenetic protein 2 or BMP2 plays an important role in the stimulation of the development of bone. For instance, it has been demonstrated to potently induce osteoblast differentiation.

Bone morphogenetic protein 7 or BMP7 plays a key role in the transformation of mesenchymal cells into bone, in particular by inducing the phosphorylation of SMAD1 and SMAD5, which in turn induce transcription of numerous osteogenic genes.

In one embodiment, the BMP2 and BMP7 content of the biomaterial of the invention may be quantified by any method known in the art, such as for example by ELISA, in particular, at 4, 5, 6, 7, or 8 weeks after addition of the biocompatible material.

In one embodiment, the level of BMP2 in the biomaterial of the invention or in supernatants of the biomaterial when in a medium is undetectable. In one embodiment, the biomaterial of the invention does not comprise substantially BMP2. In one embodiment, the ASCs of the biomaterial of the invention do not secrete substantially BMP2.

In one embodiment, the level of BMP2 is expressed in pg per mL of supernatant. In one embodiment, the biomaterial of the invention comprises or the ASCs of the biomaterial secrete less than 100 pg of BMP2 per mL, in particular, less than 85 pg/mL, or in particular, less than 75 pg/mL, or in particular, less than 62.5 pg/mL.

In one embodiment, the level of BMP7 in the biomaterial of the invention or in supernatants of the biomaterial when in a medium is undetectable. In one embodiment, the biomaterial of the invention does not comprise substantially BMP7. In one embodiment, the ASCs of the biomaterial of the invention do not secrete substantially BMP7.

In one embodiment, the level of BMP7 is expressed in pg per mL of supernatant. In one embodiment, the biomaterial of the invention comprises or the ASCs of the biomaterial secrete less than 50 pg of BMP7 per mL, in particular, less than 40 pg/mL, or in particular, less than 35 pg/mL, or in particular, less than 31.2 pg/mL.

In one embodiment, the biomaterial of the invention comprises BMP2 and/or BMP7 at concentrations as described herein above after 4, 5, 6, 7 or 8 weeks after addition of the ceramic material. In other words, in one embodiment, the biomaterial of the invention comprises BMP2 and/or BMP7 at concentrations as described herein above after 4, 5, 6, 7 or 8 weeks after the beginning of the multi-dimensional induction.

In one embodiment, the biomaterial according to the invention is mineralized. As used herein, the term "mineralization" or "bone tissue mineral density" refers to the amount of mineral matter per square centimeter of bones or "bone-like" tissues formed by biomaterial, also expressed in percentage. Accordingly, as used herein, the term "mineralization" or "bone tissue mineral density" refers to the amount of mineral matter per square centimeter of biomaterial, also expressed in percentage.

Methods to assess the mineralization degree of a biomaterial are known in the art. Examples of such methods include, but are not limited to, micro-computed tomography (micro-CT) analysis, imaging mass spectrometry, calcein blue staining, Bone Mineral Density Distribution (BMDD) analysis, and the like.

In one embodiment, the mineralization degree of the biomaterial of the invention is not less than about 1%. In one embodiment, the mineralization degree of the biomaterial of the invention is more than about 1%.

In another embodiment, the mineralization degree of the biomaterial of the invention is of at least about 5%, in particular, at least about 10%, or in particular, at least about 15%. In another embodiment, the mineralization degree of the biomaterial of the invention is of at least about 20%, in particular, at least about 25%, or in particular, at least about 30%, or in particular, at least about 35%. In one embodiment, the mineralization degree of the biomaterial of the invention is of at least about 30%, 31%, 32%, 33%, 34%, 35%, 36%, 37% or 38%.

In one embodiment, the mineralization degree of the biomaterial of the invention is ranging from about 5% to about 50%, in particular, from about 10% to about 45%, or in particular, from about 15% to about 40%. In another embodiment, the mineralization degree of the biomaterial of the invention is ranging from about 20% to about 50%, in particular, from about 25% to about 45%, or in particular, from about 30% to about 40%. In one embodiment, the mineralization degree of the biomaterial of the invention is ranging from about 35% to about 40%. In one particular embodiment, the mineralization degree of the biomaterial of the invention is of about 38%.

In one embodiment, the mineralization degree of the biomaterial of the invention is proportional to the OPG secretion. In one embodiment, the more the biomaterial comprises OPG, the more the biomaterial is mineralized.

This present invention also relates to a method for producing a multi-dimensional biomaterial comprising adipose tissue-derived stem cells (ASCs) differentiated into osteogenic cells, a ceramic material and an extracellular matrix, wherein the biomaterial comprises osteoprotegerin (OPG).

In one embodiment, the method for producing the biomaterial according to the invention comprises the steps of:
cell proliferation,
cell differentiation, and
multi-dimensional induction, e.g., 3D induction.

In one embodiment, the method for producing the biomaterial according to the invention comprises the steps of:
proliferating ASCs in vitro,
differentiating the proliferated ASCs, and
culturing the differentiated ASCs in the presence of a ceramic material.

In one embodiment, the method for producing the biomaterial of the invention further comprises a step of isolating autologous ASCs performed before the step of cell proliferation.

In one embodiment, the step of proliferation is performed in proliferation medium. In a particular embodiment, the proliferation medium is DMEM. In one embodiment, the proliferation medium is supplemented with Ala-Gln and/or human platelet lysate (hPL). In one embodiment, the proliferation medium further comprises antibiotics, such as penicillin and/or streptomycin.

In one embodiment, the proliferation medium comprises or consists of DMEM supplemented with Ala-Gln and hPL (5%). In one embodiment, the proliferation medium comprises or consists of DMEM supplemented with Ala-Gln, hPL (5%, v/v), penicillin (100 U/mL) and streptomycin (100 µg/mL).

In one embodiment, the step of proliferation is performed as described herein above. In one embodiment, the step of proliferation is performed up to P8. In one embodiment, the step of proliferation lasts up to P4, P5, P6, P7 or P8. Accordingly, in one embodiment, the step of cell proliferation includes at least 3 passages. In one embodiment, the step of cell proliferation includes at most 7 passages. In one embodiment, the step of cell proliferation includes from 3 to 7 passages. In one particular embodiment, the step of proliferation is performed up to P4. Accordingly, in one embodiment, the step of cell proliferation includes detaching cells from the surface of the culture vessel and then diluted them in proliferation medium at passages P1, P2 and P3. In an embodiment of a proliferation up to P6, the step of cell proliferation includes detaching cells from the surface of the culture vessel and then diluting them in proliferation medium at passages P1, P2, P3, P4 and P5.

In one embodiment, the step of proliferation lasts as long as necessary for the cells to be passed 3, 4, 5, 6 or 7 times. In a particular embodiment, the step of proliferation lasts as long as necessary for the cells to be passed 3 times. In one embodiment, the step of proliferation lasts until cells reach confluence after the last passage, in particular, between 70% and 100% confluence, or in particular, between 80% and 95% confluence. In one embodiment, the step of proliferation lasts until cells reach confluence after the third, fourth, fifth, sixth or seventh passage.

In an advantageous embodiment, culturing ASCs in differentiation medium before adding biocompatible particles is a key step of the method of the invention. Such a step is necessary for allowing the differentiation of the ASCs into osteogenic cells. In addition, this step is necessary for obtaining a multi-dimensional structure.

In one embodiment, the step of differentiation is performed after P4, P5, P6, P7 or P8. In one embodiment, the step of differentiation is performed when cells are not at confluence. In a particular embodiment, the step of differentiation is performed after P4, P5, P6, P7 or P8 without culture of cells up to confluence.

In one embodiment, the step of differentiation is performed at P4, P5, P6, P7 or P8. In one embodiment, the step of differentiation is performed when cells are not at confluence. In a particular embodiment, the step of differentiation is performed at P4, P5, P6, P7 or P8 without culture of cells up to confluence.

In one embodiment, the step of differentiation is performed by incubating cells in differentiation medium, in particular, osteogenic differentiation medium. In one embodiment, the step of differentiation is performed by resuspending cells detached from the surface of the culture vessel in differentiation medium, in particular, osteogenic differentiation medium.

In one embodiment, the incubation of ASCs in osteogenic differentiation medium is carried out for at least 5 days, in particular, at least 10 days, more preferably at least 15 days. In one embodiment, the incubation of ASCs in osteogenic differentiation medium is carried out from 5 to 30 days, in particular, from 10 to 25 days, or in particular, from 15 to 20 days. In one embodiment, the differentiation medium is replaced every 2 days.

In one embodiment, the step of multi-dimensional induction, in particular, 3D induction, is performed by adding a ceramic material as defined hereinabove in the differentiation medium. In one embodiment, cells are maintained in differentiation medium during the step of multi-dimensional induction, in particular, 3D induction.

In one embodiment, the step of multi-dimensional induction, in particular, 3D induction, is performed when cells reach confluence in the differentiation medium, in particular, between 70% and 100% confluence, or in particular, between 80% and 95% confluence.

In another embodiment, the step of multi-dimensional induction, in particular, 3D induction, is performed when a morphologic change appears, such as for example nodule preformation. In one embodiment, the step of multi-dimensional induction, in particular, 3D induction, is performed when at least one osteoid nodule is formed. As used herein, the term "osteoid" means an un-mineralized, organic portion of bone matrix that forms prior to the maturation of bone tissue.

In another embodiment, the step of multi-dimensional induction, in particular, 3D induction, is performed when cells reach confluence, when a morphologic change appear and when at least one osteoid nodule is formed.

In one embodiment, cells and ceramic material of the invention are incubated for at least 5 days, in particular, at least 10 days, or in particular, at least 15 days. In one embodiment, cells and ceramic material of the invention are incubated from 10 days to 30 days, in particular, from 15 to 25 days, or in particular, for 20 days. In one embodiment, the medium is replaced every 2 days during the step of multi-dimensional induction, in particular, 3D induction.

The invention also relates to a multi-dimensional biomaterial obtainable by the method according to the invention. In one embodiment, the multi-dimensional biomaterial is obtained by the method according to the invention. In one embodiment, the biomaterial obtainable or obtained by the method of the invention is intended to be implanted in a human or animal body. In one embodiment, the implanted biomaterial may be of autologous origin, or allogenic. In one embodiment, the biomaterial of the invention may be implanted in a bone or cartilage area. In one embodiment, this biomaterial may be implanted in irregular areas of the human or animal body.

In one embodiment, the biomaterial of the invention is homogeneous, which means that the structure and/or constitution of the biomaterial are similar throughout the whole tissue. In one embodiment, the biomaterial has desirable handling and mechanical characteristics required for implantation in the native disease area. In one embodiment, the biomaterial obtainable or obtained by the method of the invention can be held with a surgical instrument without being torn up.

Another object of the present invention is a medical device comprising a biomaterial according to the invention.

Still another object is a pharmaceutical composition comprising a biomaterial according to the invention and at least one pharmaceutically acceptable carrier. The term "pharmaceutically acceptable carrier", refers to biologically compatible reagents, cells, compounds, materials, compositions, and/or dosage forms which are suitable for use in contact with the tissues of human beings and animals without excessive toxicity, irritation, allergic response, or other complication commensurate with a reasonable benefit/risk ratio.

Suitable pharmaceutically acceptable carriers include water, salt solutions (e.g., saline), alcohols, oils, gelatins, and carbohydrates (e.g., lactose, amylose, or starch), fatty acid esters, hydroxymethylcellulose, and polyvinyl pyrolidine. Pharmaceutical carriers suitable for use in the present invention are known in the art and are described, e.g., in Pharmaceutical Sciences (17.sup.th Ed., Mack Pub. Co., Easton, Pa.) and WO 1996/005309, the contents of which are incorporated by reference herein.

The present invention also relates to a biomaterial or a pharmaceutical composition according to the invention for use as a medicament. The biomaterial or pharmaceutical composition may contain one or more additional bioactive drug or molecule to enhance the differentiation, survival, activity, or tolerability of the biomaterial or pharmaceutical composition. Bioactive molecules include, e.g., bone morphogenetic proteins (BMPs), vascular endothelial growth factor (VEGF), platelet-derived growth factor (PDGF), fibroblast growth factors (FGFs), and other cytokines that have either angiogenic or osteoinductive capacities.

The invention relates to any use of the biomaterial of the invention, as a medical device or included into a medical device, or in a pharmaceutical composition. In certain embodiments, the biomaterial, medical device or pharmaceutical composition of the invention is a putty-like material that may be manipulated and molded prior to use.

The present invention further relates to a method of treating a bone or cartilage defect in a subject in need thereof comprising administering to the subject a therapeutically effective amount of a biomaterial, medical device or pharmaceutical composition according to the invention. Surgical implantation into a precise location in the body is typically a suitable means of administration of the biomaterial, medical device, or pharmaceutical composition according to the invention. The biomaterial, medical device, or pharmaceutical composition may be introduced into a mammal's body in any way known in the art, including but not limited to direct implantation, surgical attachment, transplantation with other tissue, and the like.

As used herein, the term "bone defect" means a lack of bone tissue in a body area, where bone should normally be, or where formation of bone tissue is therapeutically desired.

As used herein, the term "cartilage defect" means a lack of cartilage tissue in a body area, where cartilage should normally be, or where formation of cartilage tissue is therapeutically desired.

Another object of the present invention is a biomaterial, medical device or pharmaceutical composition according to the invention for its use in the treatment of a bone or cartilage defect in a subject in need thereof. Another object of the present invention is the use of a biomaterial, medical device or pharmaceutical composition according to the invention for treating a bone defect in a subject in need thereof.

Examples of bone defect include, but are not limited to, bone fracture, bone frailty, loss of bone mineral density, arthritis, pseudarthrosis such as congenital pseudarthrosis, osteoporosis, spondylolysis, spondylolisthesis, osteomalacia, osteopenia, bone cancer, Paget's disease, sclerotic lesions, infiltrative disorders of bone, cancellous and cortical osteonecrosis, spina bifida, delayed union, osteogenesis imperfecta, cranial defect (for example after tumor resection or bleeding), osteonecrosis and metabolic bone loss.

Examples of cartilage defect include, but are not limited to, damaged cartilage or lack of cartilage in a body area. The cause of a cartilage defect can be due to trauma, osteonecrosis, osteochondritis, and other conditions. Cartilage defects are most commonly seen in the knee joint, where it is often caused by trauma and seen in association with ligament injuries, such as anterior cruciate ligament (ACL) tears.

In one embodiment, the biomaterial, medical device or pharmaceutical composition of the invention is for treating, or for use for treating, a bone defect selected from the group comprising or consisting of bone fracture, bone frailty, loss of bone mineral density, arthritis, pseudarthrosis such as congenital pseudarthrosis, osteoporosis, spondylolysis, spondylolisthesis, osteomalacia, osteopenia, bone cancer, Paget's disease, sclerotic lesions, infiltrative disorders of bone, cancellous and cortical osteonecrosis, spina bifida, delayed union, osteogenesis imperfecta, cranial defect (for example after tumor resection or bleeding), osteonecrosis and metabolic bone loss.

In one embodiment, the biomaterial, medical device or pharmaceutical composition of the invention is for treating, or for use for treating, a bone defect selected from the group comprising or consisting of bone fracture, arthritis, congenital pseudarthrosis, osteoporosis, spondylolysis, spondylolisthesis, bone cancer, Paget's disease, sclerotic lesions, cancellous and cortical osteonecrosis and metabolic bone loss.

In one embodiment, the biomaterial, medical device or pharmaceutical composition of the invention is for treating, or for use for treating, spondylolysis and/or spondylolisthesis. Spondylolysis is a defect or stress fracture in the pars interarticularis of the vertebral arch. Spondylolisthesis or slippage is the translational displacement or non-anatomic alignment of one vertebra relative to the adjacent vertebra and occurs in about 30% of patients with a spondylolysis.

In one embodiment, spondylolisthesis is dysplasic, isthmic, degenerative, traumatic, pathologic and/or post-surgical/iatrogenic spondylolisthesis. In one embodiment, spondylolisthesis is dysplasic spondylolisthesis (also called type 1), from congenital abnormalities of the upper sacral facets or inferior facets of the fifth lumbar vertebra. In another embodiment, spondylolisthesis is isthmic spondylolisthesis (also called type 2), caused by a defect in the pars interarticularis but it can also be seen with an elongated pars. In another embodiment, spondylolisthesis is degenerative spondylolisthesis (also called type 3), resulting of facet arthritis and joint remodeling. In another embodiment, spondylolisthesis is traumatic spondylolisthesis (also called type 4), resulting from acute fractures in the neural arch, other than the pars. In another embodiment, spondylolisthesis is pathologic spondylolisthesis (also called type 5), caused by either infection or a malignancy. In another embodiment, spondylolisthesis is post-surgical/iatrogenic spondylolisthesis (also called type 6), caused by complications after surgery.

In one embodiment, spondylolisthesis is of grade I, grade II, grade III, grade IV or grade V according to Myerding classification. In one embodiment, spondylolisthesis is of grade I, which corresponds to a degree of slippage from 0 to 25% as measured as percentage of the width of the vertebral body. In another embodiment, spondylolisthesis is of grade II, which corresponds to a degree of slippage from 25% to 50%. In another embodiment, spondylolisthesis is of grade III, which corresponds to a degree of slippage from 50% to 75%. In another embodiment, spondylolisthesis is of grade IV, which corresponds to a degree of slippage from 75% to 100%. In another embodiment, spondylolisthesis is of grade V, which corresponds to a degree of slippage greater than 100%.

In one embodiment, the biomaterial, medical device or pharmaceutical composition of the invention is for filling the interbody spaces and/or fusion cage(s) to be implanted in a subject in need thereof.

In one embodiment, the biomaterial, medical device or pharmaceutical composition of the invention is for treating, or for use for treating, congenital pseudarthrosis. In a particular embodiment, the biomaterial, medical device or pharmaceutical composition of the invention is for treating, or for use for treating, congenital pseudarthrosis of the tibia (CPT). CPT refers to nonunion of a tibial fracture that develops spontaneously or after a minor trauma: the tibia shows area of segmental dysplasia resulting in anterolateral bowing of the bone. CPT is usually associated with neurofibromatosis, and remains one of the most challenging and dreaded conditions confronting pediatric orthopedic surgery. Usually the disease becomes evident within a child's first year of life but may be undetected up to the age of 12 years.

In one embodiment, the CPT is of Type I, Type II, Type III or Type IV according to the Crawford classification. In one embodiment, the CPT is of Type I, corresponding to anterior bowing with an increase in cortical density and a narrow medulla. In another embodiment, the CPT is of Type II, corresponding to anterior bowing with narrow, sclerotic medulla. In another embodiment, the CPT is of Type III, corresponding to anterior bowing associated with a cyst or signs of a prefracture. In another embodiment, the CPT is of Type IV, corresponding to anterior bowing and a clear fracture with pseudarthrosis often associating the tibia and fibula.

In one embodiment, the biomaterial, medical device or pharmaceutical composition of the invention is for treating, or for use for treating, congenital pseudarthrosis of the tibia in pediatric patients. In one embodiment, the biomaterial, medical device or pharmaceutical composition of the invention is for treating, or for use for treating, pediatric congenital pseudarthrosis of the tibia.

The invention also relates to the use of the biomaterial, medical device or pharmaceutical composition of the invention in orthopedics, especially in maxillofacial or plastic surgery. The biomaterial of the invention may also be used in rheumatology.

The invention further relates to a method of using the biomaterial, medical device or pharmaceutical composition of the invention for treating, correcting or alleviating congenital or acquired abnormalities of the joints, cranio-facial-maxillary bones, orthodontic disorders, bone or articular bone disorders (for example requiring replacement) following surgery, trauma or other congenital or acquired abnormalities, and for supporting other musculoskeletal implants, particularly artificial and synthetic implants.

In another aspect, the invention relates to the biomaterial, medical device or pharmaceutical composition of the invention for use for bone reconstruction. In one embodiment, the biomaterial of the invention is for use for filling a bone cavity within the human or animal body.

In still another aspect, the invention relates to the biomaterial, medical device or pharmaceutical composition of the invention for use for reconstructive or aesthetic surgery.

In one embodiment, the invention relates to the biomaterial, medical device or pharmaceutical composition of the invention for use for reconstructive surgery. In another embodiment, the invention relates to the biomaterial of the invention for use for aesthetic surgery.

In one embodiment, the biomaterial, the medical device or the pharmaceutical composition of the invention may be used as an allogeneic implant or as an autologous implant. In one embodiment, the biomaterial, the medical device or the pharmaceutical composition of the invention may be used as a xenogenic implant. In one embodiment, the biomaterial of the invention may be used in tissue grafting.

The biomaterial of the invention is further advantageous for stimulating angiogenesis. Indeed, the ASCs of the biomaterial release vascular endothelial growth factor (VEGF) which stimulates the growth of new blood vessels.

In one embodiment, the subject is a human subject. In another embodiment, the subject is an animal subject such as for example a pet, a domestic animal or a production animal. In one embodiment, the subject is a mammal subject.

In one embodiment, the biomaterial, the medical device or the pharmaceutical composition of the invention may be used in a human and/or an animal. In one embodiment, the biomaterial, the medical device or the pharmaceutical composition of the invention may be used in human and veterinary medicine.

In one embodiment, the subject is suffering from bone and/or cartilage defect.

In a particular embodiment, the subject is suffering from spondylolysis and/or spondylolisthesis. In another particular embodiment, the subject is suffering from congenital pseudarthrosis of the tibia (CPT). In a particular embodiment, the subject is suffering from pediatric congenital pseudarthrosis of the tibia (CPT).

In one embodiment, the subject has already been treated for bone and/or cartilage defect.

In a particular embodiment, the subject has already been treated for spondylolysis and/or spondylolisthesis.

Examples of other treatments for spondylolysis and/or spondylolisthesis include, but are not limited to, conservative management such as bracing, activity restriction, extension exercises, flexion exercises and deep abdominal strengthening; and surgery such as spinal fusion, and laminectomy.

In another particular embodiment, the subject has already been treated for CPT. Examples of other treatments for CPT include, but are not limited to, bracing and surgery, such as intramedullary nailing associated with a bone graft, vascularized bone transfer, the Ilizarov technique, induced membrane and spongy autologous graft.

In one embodiment, the subject is non-responsive to at least one other treatment for bone and/or cartilage defect.

In one embodiment, the subject is an infant or a child. Accordingly, in one embodiment, the subject is a pediatric subject. In one embodiment, the subject is under 18 years, in particular, under 15 years, 12 years or 10 years.

In another embodiment, the subject is an adult. Accordingly, in one embodiment, the subject is over 18 years.

In one embodiment, the biomaterial, medical device or pharmaceutical composition of the invention is administered to the subject in need thereof during a bone and/or cartilage defect procedure, such as for example a spinal fusion procedure.

In one embodiment, the biomaterial, medical device or pharmaceutical composition of the invention is used in conjunction with debridement, placement of one or two interbody somatic cage(s) and bilateral pedicle screw fixation, and/or rehabilitation.

The invention also relates to a kit, comprising a biomaterial, a pharmaceutical composition or a medical device according to the invention and suitable fixation means. Examples of suitable fixation means include, but are not limited to, surgical glue, tissue-glue, or any adhesive composition for surgical use which is biocompatible, non-toxic, and optionally bioresorbable.

EXAMPLES

The present invention is further illustrated by the following examples.

Example 1: Production of Biomaterials of the Invention

Isolation of hASCs

Human subcutaneous adipose tissues were harvested by lipo-aspiration following Coleman technique in the abdominal region and after informed consent and serologic screening.

Human adipose-derived stem cells (hASCs) were promptly isolated from the incoming adipose tissue. Lipoaspirate can be stored at +4° C. for 24 hours or for a longer time at −80° C.

First, a fraction of the lipoaspirate was isolated for quality control purposes and the remaining volume of the lipoaspirate was measured. Then, the lipoaspirate was digested by a collagenase solution (NB 1, Serva Electrophoresis GmbH, Heidelberg, Germany) prepared in HBSS (with a final concentration of ~8 U/mL). The volume of the enzyme solution used for the digestion was the double of the volume of the adipose tissue. The digestion was performed during 50-70 min at 37° C.±1° C. A first intermittent shaking was performed after 15-25 min and a second one after 35-45 min. The digestion was stopped by the addition of MP medium (proliferation medium, or growth medium). The MP medium comprised DMEM medium (4.5 g/L glucose and 4 mM Ala-Gln; Sartorius Stedim Biotech, Gottingen, Germany) supplemented with 5% human platelet lysate (hPL) (v/v). DMEM is a standard culture medium containing salts, amino acids, vitamins, pyruvate and glucose, buffered with a carbonate buffer and has a physiological pH (7.2-7.4). The DMEM used contained Ala-Gln. Human platelet lysate (hPL) is a rich source of growth factor used to stimulate in vitro growth of mesenchymal stem cells (such as hASCs).

The digested adipose tissue was centrifuged (500 g, 10 min, room temperature) and the supernatant was removed. The pelleted Stromal Vascular Fraction (SVF) was re-suspended into MP medium and passed through a 200-500 µm mesh filter. The filtered cell suspension was centrifuged a second time (500 g, 10 min, 20° C.). The pellet containing the hASCs was re-suspended into MP medium. A small fraction of the cell suspension can be kept for cells counting and the entire remaining cell suspension was used to seed one 75 cm$^2$ T-flask (referred as Passage P0). Cells counting was performed (for information only) in order to estimate the number of seeded cells.

The day after the isolation step (day 1), the growth medium was removed from the 75 cm$^2$ T-flask. Cells were rinsed three times with phosphate buffer and freshly prepared MP medium was then added to the flask.

Growth and Expansion of Human Adipose-Derived Stem Cells

During the proliferation phase, hASCs were passaged 4 times (P1, P2, P3 and P4) in order to obtain a sufficient amount of cells for the subsequent steps of the process.

Between P0 and the fourth passage (P4), cells were cultivated on T-flasks and fed with fresh MP medium. Cells were passaged when reaching a confluence ≥70% and ≤100% (target confluence: 80-90%). All the cell culture recipients from 1 batch were passaged at the same time. At each passage, cells were detached from their culture vessel with TrypLE (Select 1X; 9 mL for 75 cm$^2$ flasks or 12 mL for 150 cm$^2$ flasks), a recombinant animal-free cell-dissociation enzyme. TrypLe digestion was performed for 5-15 min at 37° C.±2° C. and stopped by the addition of MP medium.

Cells were then centrifuged (500 g, 5 min, room temperature), and re-suspended in MP medium. Harvested cells were pooled in order to guaranty a homogenous cell suspension. After resuspension, cells were counted.

At passages P1, P2 and P3, the remaining cell suspension was then diluted to the appropriate cell density in MP medium and seeded on larger tissue culture surfaces. At these steps, 75 cm$^2$ flasks were seeded with a cell suspension volume of 15 mL, while 150 cm$^2$ flasks were seeded with a cell suspension volume of 30 mL. At each passage, cells were seeded between $0.5 \times 10^4$ and $0.8 \times 10^4$ cells/cm$^2$. Between the different passages, culture medium was exchanged every 3-4 days. The cell behavior and growth rate from one donor to another could slightly differ. Hence the duration between two passages and the number of medium exchanges between passages may vary from one donor to another.

Osteogenic Differentiation

At passage P4 (i.e., the fourth passage), cells were centrifuged a second time, and re-suspended in MD medium (differentiation medium). After resuspension, cells were counted a second time before being diluted to the appropriate cell density in MD medium, and a cell suspension volume of 70 mL was seeded on 150 cm$^2$ flasks and fed with osteogenic MD medium. According to this method, cells were directly cultured in osteogenic MD medium after the fourth passage. Therefore, osteogenic MD medium was added while cells have not reached confluence.

The osteogenic MD medium was composed of proliferation medium (DMEM, Ala-Gln, hPL 5%) supplemented with dexamethasone (1 µM), ascorbic acid (0.25 mM) and sodium phosphate (2.93 mM).

The cell behavior and growth rate from one donor to another could slightly differ. Hence the duration of the osteogenic differentiation step and the number of medium exchanges between passages may vary from one donor to another.

Multi-Dimensional Induction of ASCs

The multi-dimensional induction of ASCs was launched when cells reach a confluence and if a morphologic change appears and if at least one osteoid nodule (i.e., the unmineralized, organic portion of the bone matrix that forms prior to the maturation of bone tissue) was observed in the flasks.

After being exposed to the osteogenic MD medium, the culture vessels containing the confluent monolayer of adherent osteogenic cells were slowly and homogeneously sprinkled with various ceramic materials:

HA/β-TCP particles: in a ratio of 65/35, 1.5 cm$^3$ for a 150 cm$^2$ flask (Teknimed, France),
HA particles: 1.5 cm$^3$ for a 150 cm$^2$ flask (Biocetis, France), or
β-TCP particles: 1.5 cm$^3$ for a 150 cm$^2$ flask (Biocetis, France).

Cells were maintained in MD medium. Regular medium exchanges were performed every 3 to 4 days during the multi-dimensional induction. Those medium exchanges were performed by carefully preventing removal of ceramic material particles and developing structure(s).

Example 2: Characterization of the Biomaterials

Materials and Methods

Cytotoxicity

The objective of this method was to evaluate the toxicity of an indirect cell-material contact (diffusion of leachable chemicals in the culture medium). In this method, hASCs were seeded with 8000 cells/cm$^2$ (15200 cells per well) and incubated at 37° C. in two 24-well plates for 72 hours. Then, when cells were at confluence, culture medium was removed and the ceramic material was loaded into transwell inserts containing a bottom microporous membrane:

three different quantities of HA/β-TCP: 1.5 cm$^3$, 2.85 cm$^3$ and 5.91 cm$^3$ for a vessel of 150 cm$^2$,
1.5 cm$^3$ of HA particles for a vessel of 150 cm$^2$, or
1.5 cm$^3$ of β-TCP particles for a vessel of 150 cm$^2$, and then placed into each individual well and incubated at 37° C./5% CO2 for 24 hours.

After incubation, cell viability was evaluated using the "CCK-8 kit" for quantitation of viable cell number in proliferation and cytotoxicity assays (Sigma), according to the supplier's instructions. Briefly, culture medium was removed and a volume of 100 µL of the CCK-8 solution was added to each well of the plate. The mixture was incubated at 37° C./5% CO2 for 2 to 4 hrs. The stable tetrazolium salt is cleaved to a soluble formazan dye by a complex cellular mechanism. This bioreduction is largely dependent on the glycolytic production of NAD(P)H in viable cells. Therefore, the amount of formazan dye formed directly correlates to the number of metabolically active cells in the culture. The amount of formazan dye is evaluated by measuring an optical density (OD) at 450 nm using a spectrophotometer plate reader.

The relative cell viability (%) was expressed as a percentage relative to the untreated control cells. It was determined as follows:

$$\text{Relative cell viability} = \frac{(OD - \text{blank})_{treated}}{(OD - \text{blank})_{untreated}} \times 100$$

(OD—blank)$_{untreated}$: average of (OD—blank) of negative control (untreated cells).

Cells not sprinkled with a ceramic material were used as negative control (untreated cells). Cells treated with a solution of Triton 1% were used as positive control.

Histological Analysis

Biopsies of structures formed in MD medium were taken at 4 weeks and 8 weeks after addition of ceramic particles.

Structure/Cellularity/Presence of Extracellular Matrix

The structure of the tissue, cellularity and the presence of extracellular matrix were assessed after hematoxylin-eosin and Masson's Trichrome staining.

Osteo-Differentiation and Mineralization

The osteo-differentiation and the mineralization of the tissues were assessed on osteocalcin and micro-CT respectively.

Acquisitions were carried out using a Skyscan 1172G (Bruker) (Erwan Plougonven, ULg, Liege). The reconstructions were performed on NRecon, v. 1.6.10.1, the Bruker microCT software. After adjustments, 3D images around 1700×1700×700 voxels (3D pixels) were reconstructed. With the resolution indicated above, the volume of a voxel is 985 µm$^3$. The average volume and thickness measurements of attenuating areas were reported in % of total volume. Attenuating areas were assimilated to the mineralized areas.

Growth Factors Content

To assess the bioactivity of the tissue formed, biopsies were taken at 4 and 8 weeks post-addition of ceramic particles for proteins extraction and quantification. The total protein and growth factors contents were quantified by colorimetry (BCA Protein Assay Kit, ThermoFisher Scientific) and ELISA for BMP2, BMP7, VEGF, SDF1α, IGF1 (Human Quantikine ELISA kits, RD Systems), according to suppliers' instructions.

Osteoclastic Activity

Supernatants from ASCs in 2D culture (in MD medium or MP medium) and from ASCs in multi-dimensional culture induced by addition of HA/βTCP during about 8 weeks, were harvested after 72 hours of culture in hPL-free conditions and directly stored at −20° C. for further quantification. Proteins of ceramic particles alone were also extracted to quantify OPG and RANKL levels.

OPG and RANKL were quantified using ELISA kits (Human TNFSF11/RANKL/TRANCE ELISA Kit; Human Osteoprotegerin ELISA Kit; LS Bio), according to supplier's instructions.

Results

Cytotoxicity

At low concentration (10 mg/cm$^2$), indirect contact of hASCs with HA/β-TCP particles improved cells viability (111.1% of cells viability, compared to cells alone). In contrast, concentrations of 19 and 39.4 mg/cm$^2$ decreased cells viability of 10 and 52.3%, respectively (FIG. 1).

Histological Analysis

No significative difference was found between structures after 4 weeks or 8 weeks of incubation with biocompatible particles.

Structure/Cellularity/Presence of Extracellular Matrix

A few days after the addition of the ceramic material, the osteogenic cells and the dispersed ceramic material particles become progressively entombed in mineralizing extracellular matrix.

Thereafter, the osteogenic cells and the ceramic material particles start forming a large 3-dimensional patch (or few smaller patches) of partially mineralized brownish-yellow moldable putty detaching from each culture vessels. After about 15 days, the multi-dimensional biomaterial has developed and may be detached from the flasks.

Figure 2A:
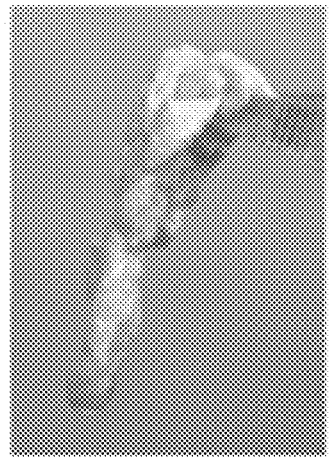
FIGS. 2A-2C are a set of photographs showing a macroscopic view of a biomaterial formed with HA/β-TCP (FIG. 2A), HA (FIG. 2B) or β-TCP (FIG. 2C).
Figure 2B:
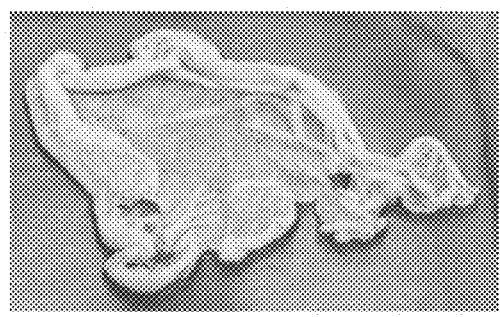
Figure 2C:
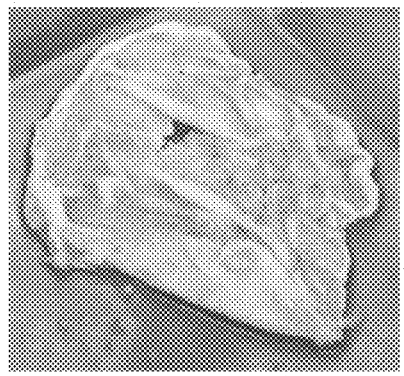
Figure 3:
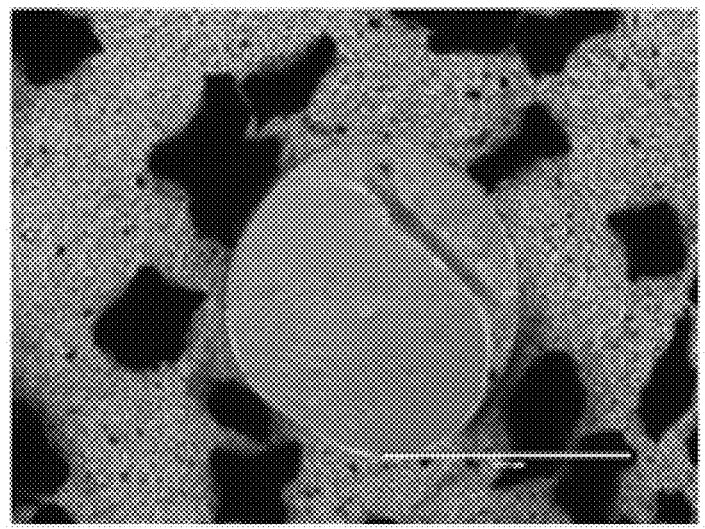
FIG. 3 is a set of photographs showing a microscopic view of a biomaterial formed with HA/β-TCP.

The co-culture of hASCs and any of the different particles (HA/β-TCP, HA and β-TCP) in osteogenic differentiation medium showed the formation of a multi-dimensional structure. This structure was prehensile with forceps and resistent to mechanical strenghts (FIGS. 2A-2C). FIG. 3 shows a microscopic view of the biomaterial formed with HA/β-TCP.

A cellularity of 262±205 cells/mm$^2$ was found for biomaterial formed with HA/β-TCP (n=7).

Figure 4A:
FIGS. 4A-4C are a set of photographs showing a hematoxylin-eosin (FIG. 4A), Masson's trichome (FIG. 4B), and osteocalcin (FIG. 4C) stainings of a biomaterial formed with HA/β-TCP.
Figure 4B:
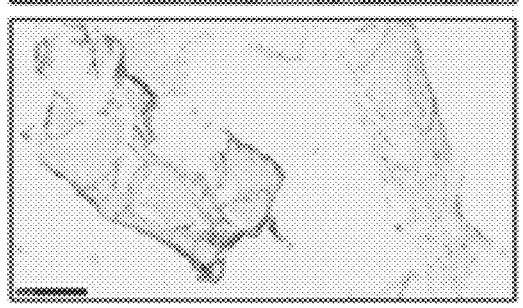

Histological analysis by hematoxylin-eosin and Masson's trichome staining revealed the presence of interconnected tissue between cells and particles and that particles are integrated in the cellularized interconnective tissue (FIGS. 4A-4B).

Osteo-Differentiation/Mineralization

Figure 4C:
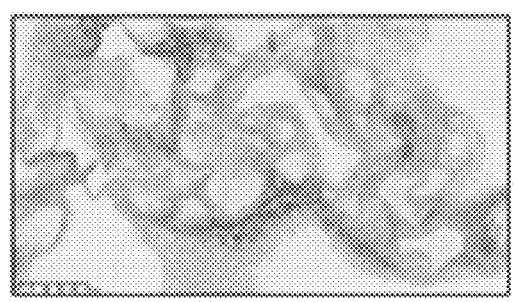

Osteocalcin staining was positive in the extracellular matrix (FIG. 4C), showing a proper differentiation of ASCs into osteogenic cells.

Figure 5A:
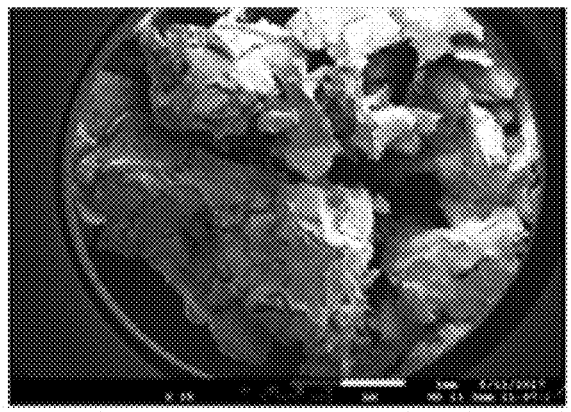
FIGS. 5A-5C are a set of photographs showing Micro-CT analysis on a biomaterial formed with HA/β-TCP at three different scales.
Figure 5B:
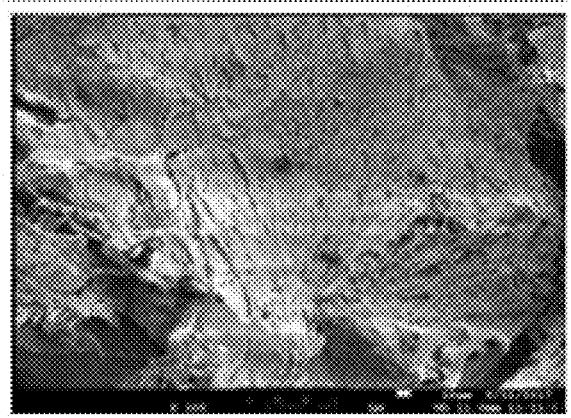
Figure 5C:
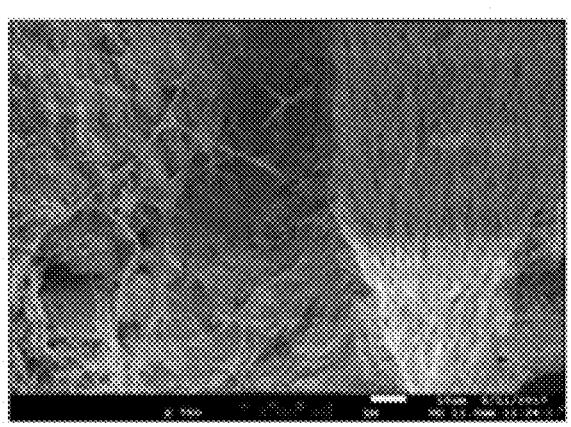

Micro-CT analysis revealed a mineralization degree of 1.9% for biomaterial formed with HA/β-TCP (FIGS. 5A-5C).

Growth Factor Content

No significative difference was found between structures after 4 weeks or 8 weeks of incubation with biocompatible particles.

Figure 6:
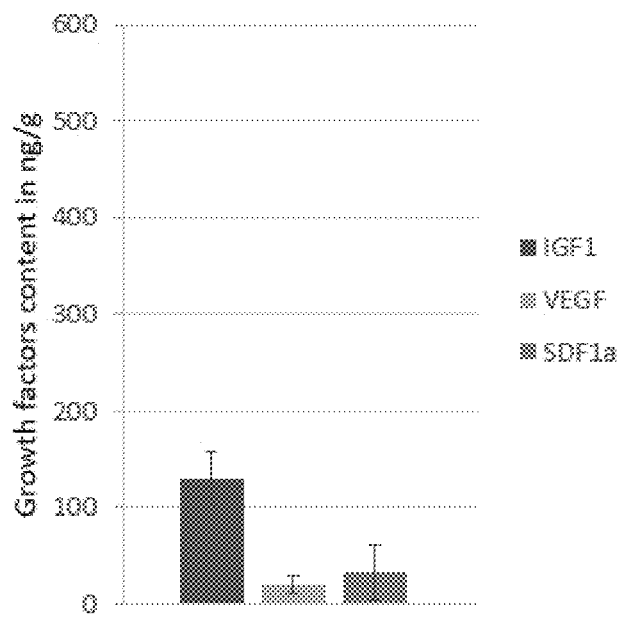
FIG. 6 is a histogram showing IGF1 (dark grey), VEGF (light grey) and SDF-1 (mid-grey) content of a biomaterial formed with HA/β-TCP.

Results are presented in below Table 1 and in FIG. 6.

TABLE 1

| Growth factor content (in ng/g of biomaterial) | | | |
|---|---|---|---|
| | VEGF | IGF1 | SDF-1α |
| HA/β-TCP | 34 ± 57 | 94 ± 57 | 31 ± 24 |
| HA | 96.88 | 99.58 | 40.63 |
| β-TCP | 75.28 | 89.78 | 51.70 |

All biomaterials formed with ceramic particles of the invention comprises VEGF, IGF1 and SDF-1α. The content in SDF-1α is lower than those of VEGF and IGF1. No BMP2 or BMP7 were detected in all tissues.

Osteoclastic Activity

OPG/RANKL secretion were quantified in the supernatant of hASCs in MP/MD media, biomaterials formed with HA/β-TCP, biomaterials formed with HA and biomaterials formed with β-TCP.

No RANKL was detected. No OPG was found in the supernatant of cells in MP or MD media.

Figure 7:
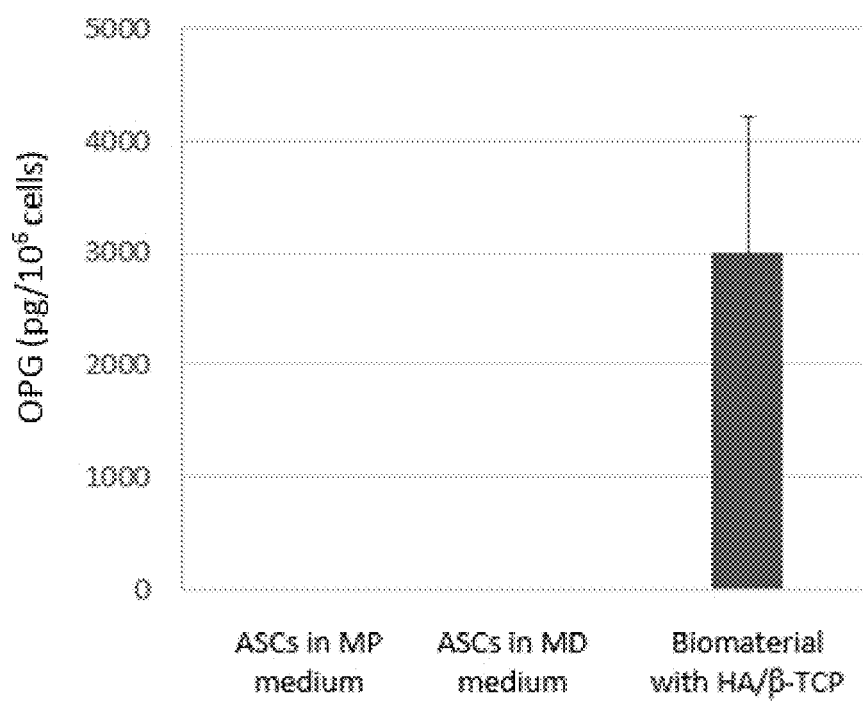
FIG. 7 is a histogram showing OPG secretion by ASCs in pg per 10$^6$ cells in 2D culture in MP medium and in MD medium, and in culture medium of a biomaterial formed with HA/β-TCP.

In contrast, biomaterials formed with HA/β-TCP secrete about 3010 pg/10$^6$ cells (FIG. 7). In terms of concentrations per gram of tissue, biomaterials formed with HA/β-TCP about 30 ng/g, biomaterials formed with HA about 76 ng/g and biomaterials formed with β-TCP about 84 ng/g (FIG. 8).

OPG secretion by HA/β-TCP alone was also assessed and found at nearly undetectable levels (FIG. 8).

Example 3: Osteogenic and Angiogenic Potential

Materials and Methods

Total RNA was extracted from ASCs in proliferation medium (MP) (n=4, from 4 different human adipose tissue donors), ASCs in differentiation medium (MD, cells cultured in a classical osteogenic media without particles) (n=4, from 4 different human adipose tissue donors) and biomaterial formed with 1.5 cm$^3$ HA/β-TCP (n=4, from 4 different human adipose tissue donors) using the Qiazol lysis reagent (Qiagen, Hilden, Germany) and a Precellys homogenizer (Bertin instruments, Montigny-le-Bretonneux, France). RNAs were purified using Rneasy mini kit (Qiagen, Hilden, Germany) with an additional on column DNase digestion according to the manufacturer's instruction. Quality and quantity of RNA were determined using a spectrophotometer (Spectramax 190, Molecular Devices, California, USA). cDNA was synthesized from 0.5 µg of total RNA using RT$^2$ RNA first strand kit (Qiagen, Hilden, Germany) for osteogenic and angiogenic genes expression profiles though commercially available PCR arrays (Human RT$^2$ Profiler Assay—Angiogenesis; Human RT$^2$ Profiler Assay—Osteogenesis, Qiagen). The ABI Quantstudio 5 system (Applied Biosystems) and SYBR Green ROX Mastermix (Qiagen, Hilden, Germany) were used for detection of the amplification product. Quantification was obtained according to the ΔΔCT method. The final result of each sample was normalized to the means of expression level of three Housekeeping genes (ACTB, B2M and GAPDH).

Expression of osteogenic and angiogenic genes at the mRNA level was performed using real-time RT-PCR (human RT2 Profiler Array, Qiagen).

Results

Among the 84 osteogenic genes tested, 11 genes involved in the skeletal development (ACVR1, BMPR1A, BMPR1B, BMPR2, CSF1, EGFR, FGFR1, IGFR1, RUNX2, TGFBR1, TWIST1), 3 transcription factors (SMAD2, SMAD4, SMAD5), 2 growth factors (VEGFA, VEGFB) and 3 cell adhesion molecules (ITGA1, ITGB1, ICAM1) were found modulated in the biomaterial of the invention in comparison with ASC in MP or ASC in MD (FIGS. 9A-9H).

Figure 9C:
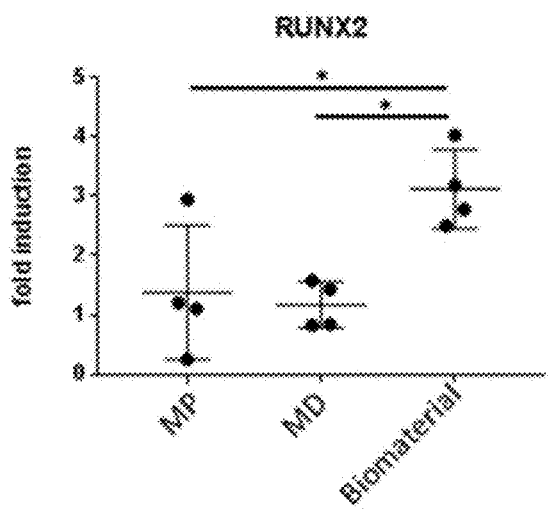

Runt-related transcription factor 2 (Runx2), an essential osteogenesis specific transcription factor which promotes the expression of osteogenesis related genes, regulates cell cycle progression, improves bone microenvironment and affects functions of chondrocytes and osteoclasts (Bruderer M et al, Eur Cell Mater, 2014; Xu J et al, Am J Trans Res, 2015), was significantly higher expressed in the biomaterial of the invention in comparison to ASCs in MP or MD (FIG. 9C).

Figure 9D:
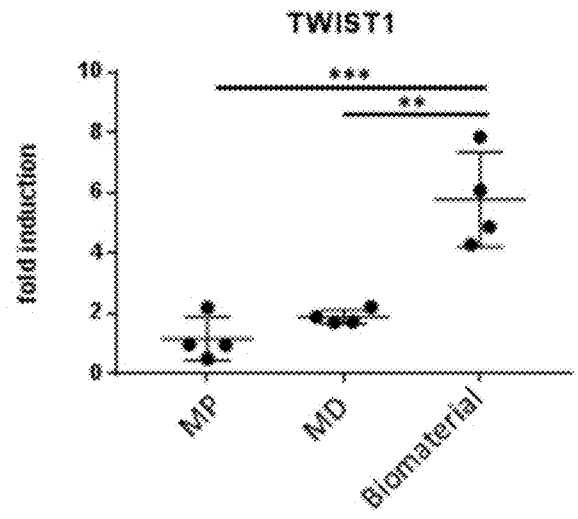
Figure 9E:
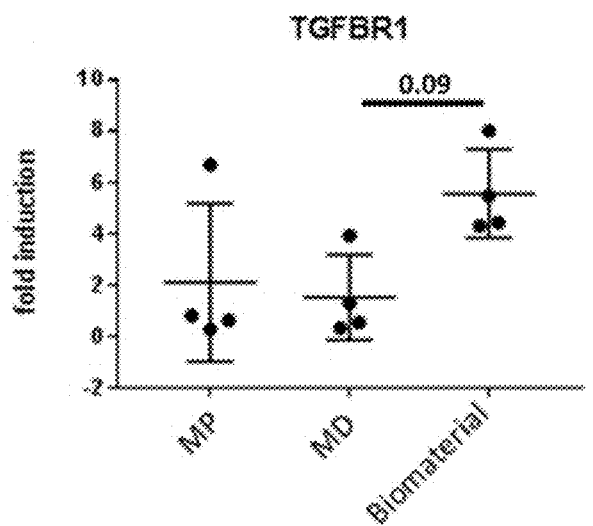
Figure 9F:
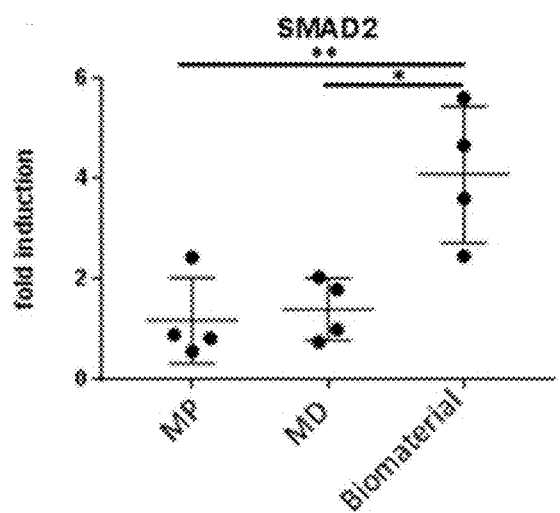
Figure 9G:
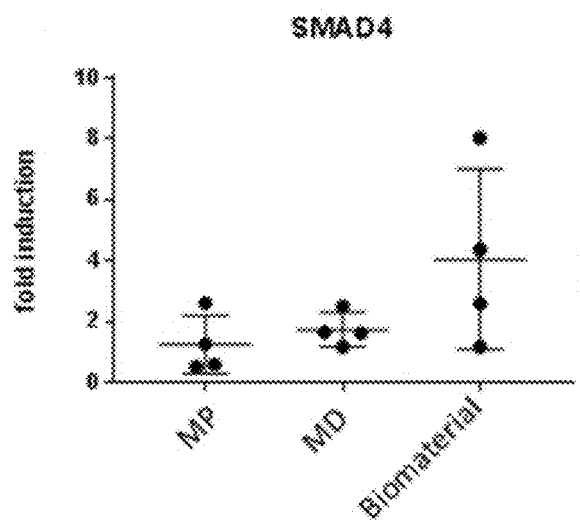
Figure 9H:
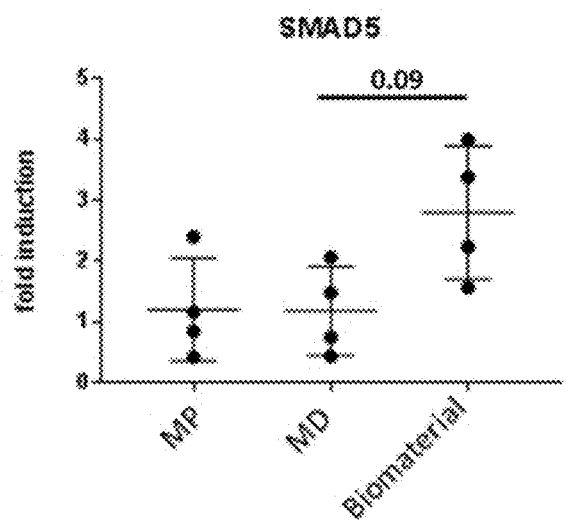

TWIST-related protein 1 (TWIST1), expressed in the skeletal mesenchyme and playing key roles in the control of mesenchymal cell lineage allocation during skeletal development (Johnson D et al. Mech Dev. 2000; Rice D P, et al. Mech Dev. 2000), was also significantly higher expressed in the biomaterial of the invention in comparison to ASCs in MD (p=0.09) (FIG. 9D).

An important pathway of osteogenesis is the Transforming Growth Factor-beta/Bone Morphogenetic protein (TGF-b/BMP) pathway. TGF-b (through TGFBR1 activation) activates the intracellular signaling proteins such as SMADs. These factors modulate the transcription of the TGF-beta-regulated genes and thereby activate osteogenic gene transcription, promoting the osteoblastic differentiation (Song B, Cytokine Growth Factor Rev. Author, 2010). Interestingly, a higher expression of TGFBR1 and SMAD2/5 mRNA was found in the biomaterial of the invention in comparison with ASCs in MD (FIG. 9E-H).

Among the 84 angiogenic genes tested for ASCs in MP, MD and biomaterial of the invention, 6 genes were related to growth factors (ANG, EFNA1, EFNB2, VEGFA, FGF1, TGFB1), 2 ECM molecules (LEP, TIMP1) and 2 cell adhesion molecules (ENG, THBS1) were modulated (FIG. 10).

A significant higher expression of angiopoietin (ANG) mRNA was found in the biomaterial of the invention in comparison with ASCs in MP (FIGS. 10A-10F). Angiopoietin signaling promotes angiogenesis, the process by which new arteries and veins form from preexisting blood vessels (Fagiani E et al, Cancer Lett, 2013).

Figure 10A:
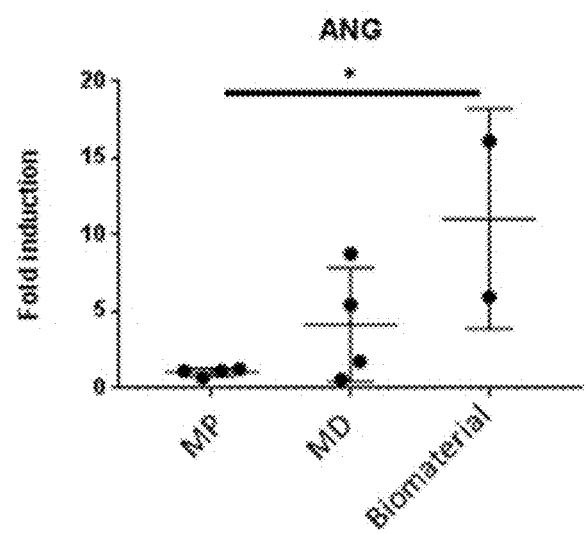
FIGS. 10A-10F are a set of graphs showing expression of genes ANG (FIG. 10A), EFNA1 (FIG. 10B), EFNB2 (FIG. 10C), VEGFA (FIG. 10D), FGF1 (FIG. 10E), LEP (FIG. 10F) in the biomaterial of the invention formed with HA/β-TCP (biomaterial) compared to ASCs in MP (MP) and in MD (MD). *: $p<0.05$, **: $p<0.01$.
Figure 10B:
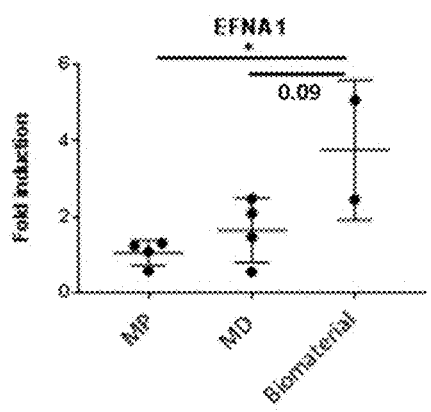
Figure 10C:
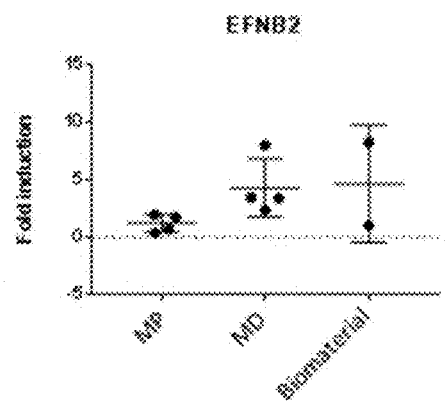

Moreover, the Ephrin A1 (EFNA) mRNA, which regulates angiogenesis in embryonic development and in the adult tissues (Pasquale et al. Nat. Rev. Mol. Cell Biol. 2005, 6(6):462-475), was found to be highly expressed in the biomaterial of the invention in comparison to ASCs in MP and MD (FIGS. 10B and 10C).

Figure 10D:
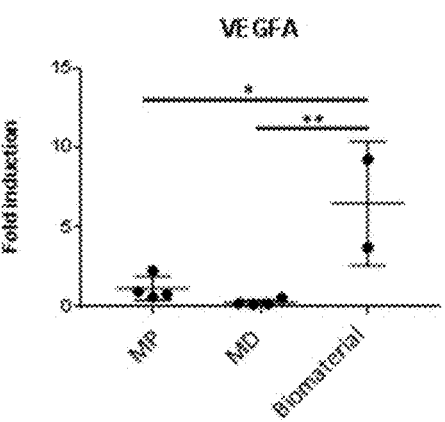

The expression of the vascular endothelial growth factor A mRNA (VEGFA) was also significantly improved for ASCs in the biomaterial of the invention in comparison to ASCs in MP or MD (FIG. 10D). VEGF is one of the most important growth factors for the regulation of vascular development and angiogenesis. Since bone is a highly vascularized organ (with the angiogenesis as an important regulator in the osteogenesis), the VEGF also positively impacts the skeletal development and postnatal bone repair (Hu K et al, Bone 2016).

Figure 10E:
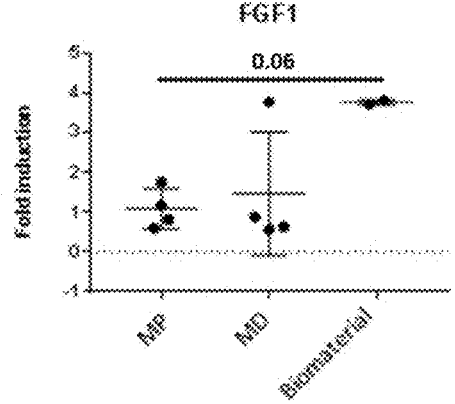
Figure 10F:
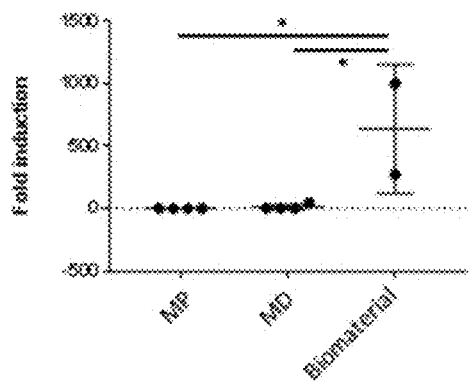

The expression of the Fibroblast growth factor 1 (FGF1) mRNA, (a potent pro-angiogenic factor, Murakami M et al, Curr Opin Hematol 2009) and the Leptin (LEP) mRNA (an important enhancer of angiogenesis and inducer of the expression of VEGF; Bouloumie A et al, Circ. Res. 1998; Sierra-Honigmann M R et al, Science (New York, N.Y.) 1998) was also over-expressed in the biomaterial of the invention in comparison to ASCs in MP (FIGS. 10E and 10F respectively).

In conclusion, the biomaterial of the invention can be defined as osteogenic by the presence of cells (in the 3D-structure) expressing, at the molecular levels, the capacity of osteo-differentiation and also the capacity to promote angiogenesis for cellular engraftment after transplantation.

Example 4: Promotion of the Vascularization and Osteogenesis in a Fibrotic Environment after Transplantation 4.1. In Vitro One of the most common elements of tissue injury is the presence of hypoxia. Interstitial damage is often associated with activation of the coagulation cascade, resulting in areas of hypoxia. In this context, we assessed the capacity of the biomaterial of the invention to secrete the VEGF, a key growth factor for the vascularization post-transplantation (Madrigal M et al., J Transl Med. 2014 Oct. 11; 12:260). It is known that reduction in oxygen tension in a variety of tissues leads to activation of the hypoxia inducible factor (HIF-1α), which induces transcription of angiogenic genes such as vascular endothelial growth factor (VEGF) (Ahluwalia A et al., Curr Med Chem. 2012; 19(1):90-97; Hawkins K E et al., Regen Med. 2013; 8(6):771-782), as well as the MSC chemoattractant stromal cell-derived factor 1 (SDF-1α) (Youn S W et al., Blood. 2011; 117:4376-4386. Ceradini D J et al., Nat Med. 2004; 10(8):858-864).

Materials and Methods

To assess the impact of low oxygen concentration on the pro-angiogenic properties of the biomaterial, biomaterial formed with ASCs from 3 donors and 1.5 cm$^3$ HA/β-TCP were washed twice with PBS and incubated in duplicate in 6 wells-plates in 10 mL of osteogenic differentiation medium (MD) without hPL (to avoid exogenous growth factors in the medium). Plates were placed in hypoxia (1% O2) or normoxia (21% O2), 5% CO2, 37° C., for 72 hours. Supernatants were then harvested for VEGF and SDF-1α quantification by ELISA.

In addition, confluent ASCs at passage 4 from 3 donors in duplicate in 6 wells-plates were washed twice with PBS and placed in 5 or 10 mL of proliferation medium (MP) or osteogenic differentiation medium (MD) without hPL in hypoxia (1% $O_2$) or normoxia (21% $O_2$), 5% $CO_2$, 37° C., for 72 hours. Supernatants were then harvested for VEGF as well as SDF-1α quantification by ELISA.

Results

While the VEGF secretion by cells in 2D (MP and MD) was increased at low oxygen tension (242±51 vs 29±27 pg/10$^5$ cells in MP and 565±507 vs 182±216 pg/10$^5$ cells in MD at 1 vs 21% O2, respectively (p<0.05)), no impact of hypoxia on the VEGF secretion was found for the biomaterial of the invention (760±594 vs 806±530 pg/10$^5$ cells at 1 vs 21% O2, respectively) (FIG. 11A). Therefore, low oxygen tension is not a limiting factor to the use of the biomaterial of the invention.

In addition, a higher VEGF secretion was found in the biomaterial of the invention in comparison to ASCs in MP and MD at both 1 and 21% O2 conditions (FIG. 11A).

While a stimulation of the SDF-1α secretion was observed for ASCs in MD after the hypoxic challenge (p=0.009), a significant higher amount of SDF-1α was released by the biomaterial of the invention in comparison to ASCs in MP and MD at 21% O2 (p=0.013 and 0.025, respectively) (FIG. 11B).

In addition, a lower secretion was demonstrated for ASCs MD in comparison to ASCs MP and the biomaterial of the invention at 1% O2 (p=0.009 and 0.013, respectively) (FIG. 11B).

The exposition of the biomaterial of the invention to a low oxygen tension (at 1% oxygen as found in a fibrotic tissue) revealed the capacity of ASCs to secrete the key effectors of vasculogenesis. These secretions were better (at both hypo- and normoxia) for ASCs in 3-dimension with extracellular matrix, i.e. in the biomaterial of the invention, in comparison to ASCs in proliferation/osteogenic media cultured in 2-dimension.

4.2. In Vivo

In view to determine the bioactivity of the biomaterial of the invention in hypoxic condition, a preclinical model of muscular necrosis was performed. The heterotopic model, illustrated by Schubert et al. (Biomaterials, 2011; 32(34): 8880-91), is a gold standard model to investigate the bioactivity of biomaterials and consists in the implantation of a test-item (biomaterials) in the lumbar area, in a pocket constituted by the cauterized paravertebral muscle.

Materials and Methods

Two experiments were realized on nude rats to allow the implantation of the biomaterial of the invention (human origin) avoiding any graft rejection.

The first experiment was designed to assess the role of the biomaterial of the invention on the tissue remodeling at 1-month post-implantation. The second experiment was designed to assess at the molecular level the tissue remodeling (at day 29 post-implantation).

In both experiments, the biomaterial was implanted bilaterally in 10 nude rats. The volume implanted was approximately 0.3 cm$^3$ (corresponding to 500 mg or 4.7*10$^6$ cells) of the biomaterial.

In the first experiment, at day 28 post-implantation, the angiogenesis was quantified by histomorphometry following immunostaining for von Willebrand, and the presence of human cells was assessed by an immunohistochemistry for HLA.

In the second experiment, at day 29 post-implantation, the presence of human cells was assessed by an immunohistochemistry for HLA and the revascularization of the implants was assessed by histomorphometry analysis following a Masson's trichrome staining.

Moreover, total RNA was extracted from explants using the Qiazol lysis reagent (Qiagen, Hilden, Germany) and a Precellys homogenizer (Bertin instruments, Montigny-le-Bretonneux, France). RNAs were purified using Rneasy mini kit (Qiagen, Hilden, Germany) with an additional on column DNase digestion according to the manufacturer's instruction. Quality and quantity of RNA were determined using a spectrophotometer (Spectramax 190, Molecular Devices, California, USA). cDNA was synthesized from 0.5 µg of total RNA using RT$^2$ RNA first strand kit (Qiagen, Hilden, Germany) for osteogenic and angiogenic genes expression profiles though commercially available PCR arrays (Human RT$^2$ Profiler Assay—Angiogenesis; Human RT$^2$ Profiler Assay—Osteogenesis, Qiagen). The ABI Quantstudio 5 system (Applied Biosystems) and SYBR Green ROX Mastermix (Qiagen, Hilden, Germany) were used for detection of the amplification product. Quantification was obtained according to the ΔΔCT method. The final result of each sample was normalized to the means of expression level of three Housekeeping genes (ACTB, B2M and GAPDH).

The osteogenic genes expression was compared between the explants obtained from biomaterial of the invention at day 29 post-implantation. Eighty-four osteogenic genes were then tested for the explant.

Results

First Experiment

Figure 12:
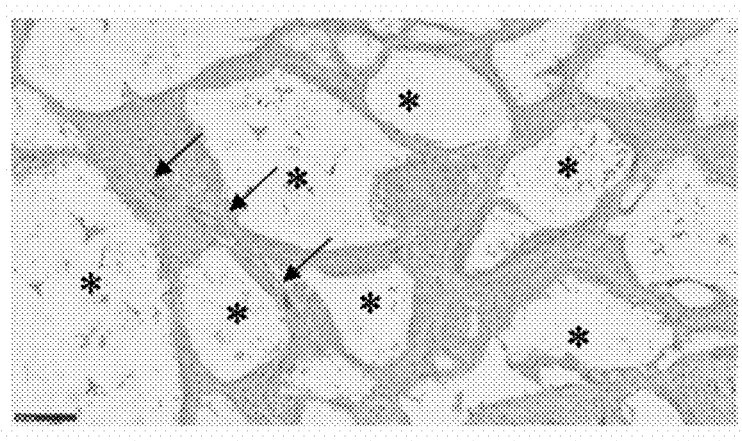
FIG. 12 is a photograph showing immunostaining for von Willebrand factor of explants from a biomaterial of the invention. HA/β-TCP particles are indicated by the symbol * and the vessels by black arrows.

The presence of vascular ingrowth was confirmed inside the biomaterial at 1-month post-implantation (FIG. 12).

Figure 13A:
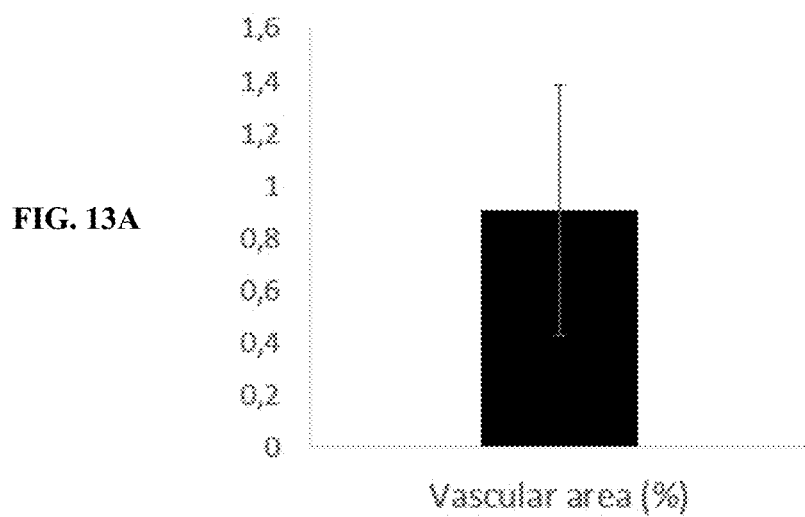
FIGS. 13A-13B are a set of histograms showing vascular area in percentage (FIG. 13A) and number of vessels/mm$^2$ (FIG. 13B) in biomaterials of the invention.
Figure 13B:
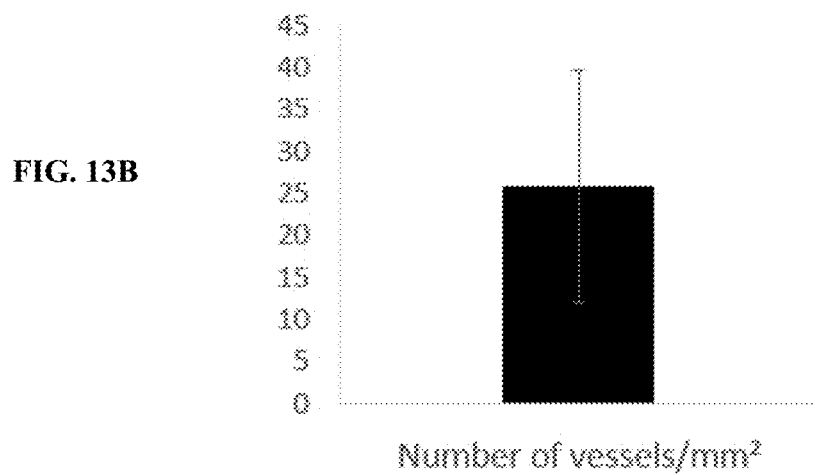

The results of the blood vessels surface area and the number of vessels/mm$^2$ are presented in FIGS. 13A-13B.

Figure 14:
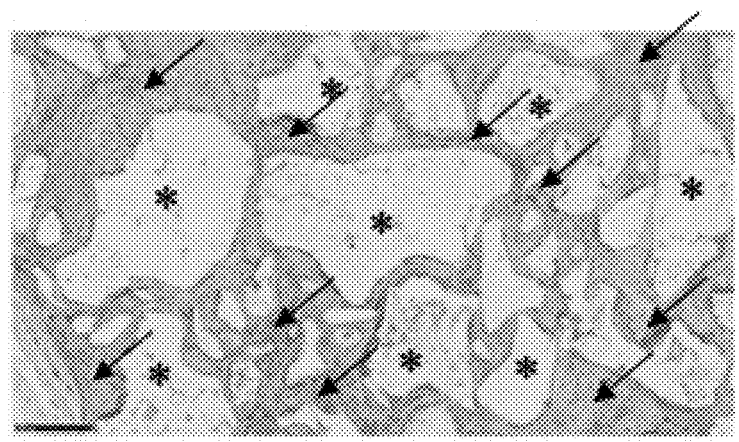
FIG. 14 is a photograph showing presence of human cells revealed by HLA/Human Leucocyte Antigen immunostaining in brown by a peroxidase revelation (indicated here by black arrows) in biomaterials of the invention at day 28 post-implantation in rats. HA/β-TCP particles are indicated by the symbol *.

The presence of human cells into biomaterials of the invention demonstrated the capacity of human ASCs in biomaterials of the invention to survive into a necrotic host tissue (as followed by the cauterization of the muscular area/implantation site) (FIG. 14).

Second Experiment

At day 29 post-implantation, the presence of human cells was demonstrated in biomaterial of the invention (data not shown).

As previously described in the first experiment of bioactivity, the revascularization of the implants was confirmed at day 29 post-implantation (data not shown).

The in vivo experiments revealed the capacity of the biomaterial of the invention to induce angiogenesis inside the product.

Example 5: Treatment of Bone Defect

To study the efficacy of the biomaterial of the invention in bone formation, a critical-sized bone defect in a rat model was designed. This model is well described in the literature (Saxer et al., Stem Cells 2016—Manassero et al., Journal of Visualized Experiments 2016).

Materials and Methods

Male nude rats were selected as recipients of human biomaterial of the invention to avoid any T-cells immune reaction. Briefly, a critical-sized bone defect in the femur of rats by using the RatFix System® (RISystem—Switzerland) was performed in 14 nude rats (2 groups of 7 recipients for HA/β-TCP particles alone and biomaterial, respectively). A defect of 5 mm was produced and the two segments of the femur were joined by the application of a plate fixed with screws.

Three weeks after the bone defect induction, a radiography was performed to assess the irreversibility of the bone defect and to avoid any spontaneous bone regeneration.

Nude rat recipients (with the persistence of the bone defect and without any fixation material breakage) were implanted with HA/β-TCP particles (for a total volume of 0.344 cm$^3$ corresponding to 500 mg) or with biomaterial of the invention formed with ASCs and 1.5 cm$^3$ of HA/β-TCP particles (for a total volume of 0.313 cm$^3$ corresponding to 500 mg with 4.7*10$^6$ cells).

At 1-month post-implantation, microCT-scan and histology were performed for each animal in view to assess the level of implant integration and bone fusion.

Results

Figure 15:
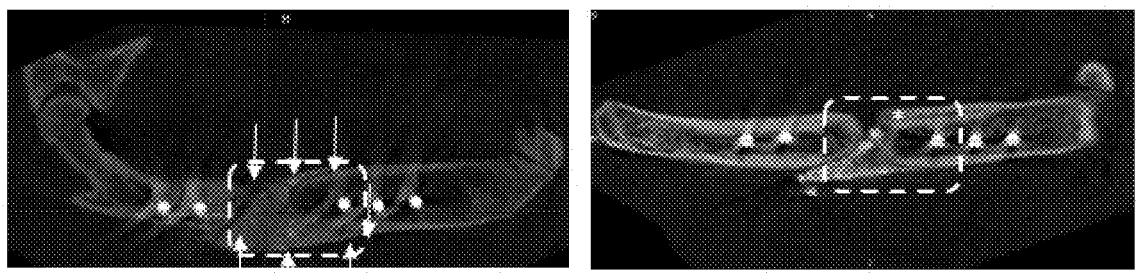
FIG. 15 is a set of photographs showing microCT-scan of the femur at 1-month post-implantation in rats of the biomaterial of the invention (upper and lower left) and HA/β-TCP particles alone (upper and lower right). Lower photographs are enlargements of upper photographs. Dot rectangles represent sites of implantation.
Figure 15:
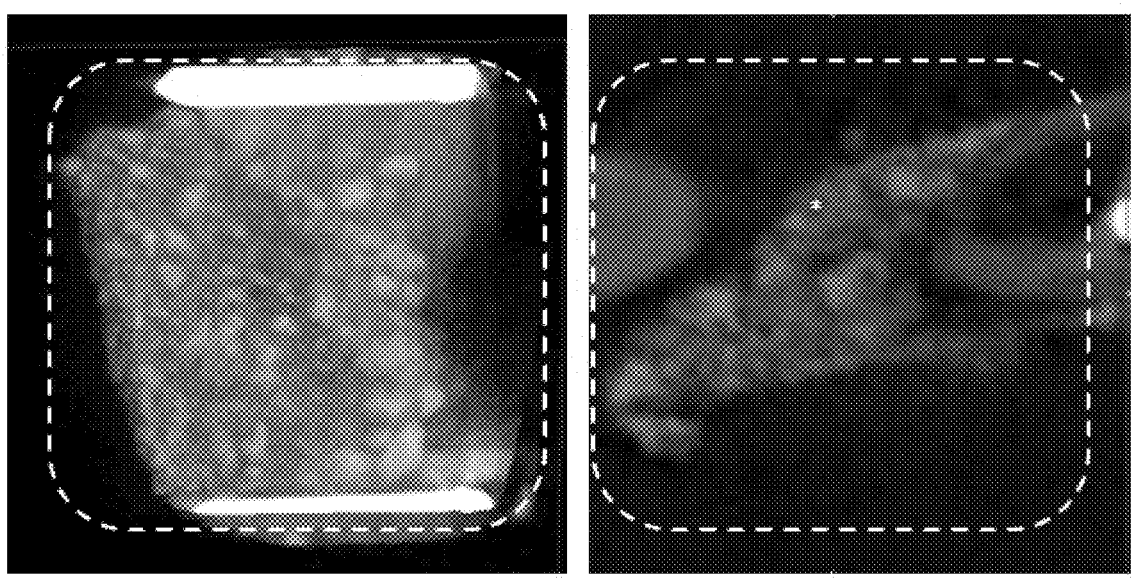

At 1-month post-implantation, the biomaterial of the invention was totally integrated between the both segments of the femur to perform a bi-cortical bone fusion (continuity of the 2 femoral cortical structures) (FIG. 15, upper and lower left) while HA/β-TCP particles alone were located in the bone defect without any integration (FIG. 15, upper and lower right). Indeed, no bridge between the cortical bones and HA/β-TCP particles was found without bilateral cortical fusion (as indicated with the symbol * in FIG. 15, lower right) and atrophic aspect of femoral defect extremities.

Figure 16A:
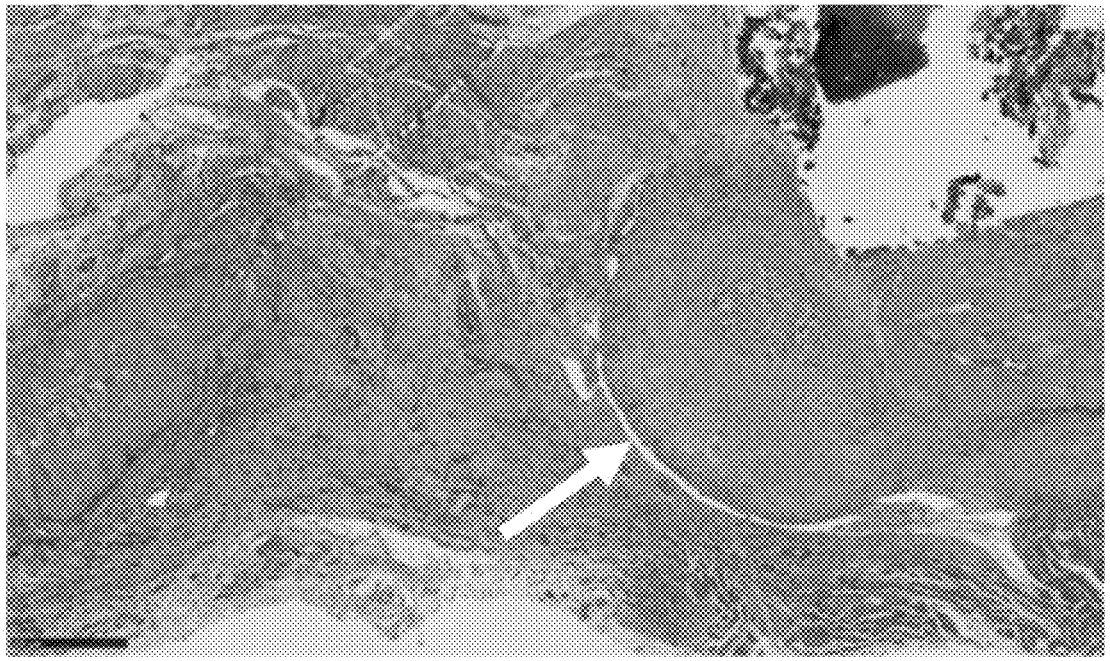
FIGS. 16A-16B are a set of photographs showing histology of bone defect 1 month after implantation of HA/β-TCP particles: haematoxylin-eosin staining, original magnification ×5 (FIG. 16A); Masson's trichrome staining, original magnification ×20 (FIG. 16B). White arrow represents the non-integration of the product and an important fibrosis. Black arrow indicates the absence of endochondral ossification in the defect at the interface between the native bone and the implant of HA/β-TCP.
Figure 16B:
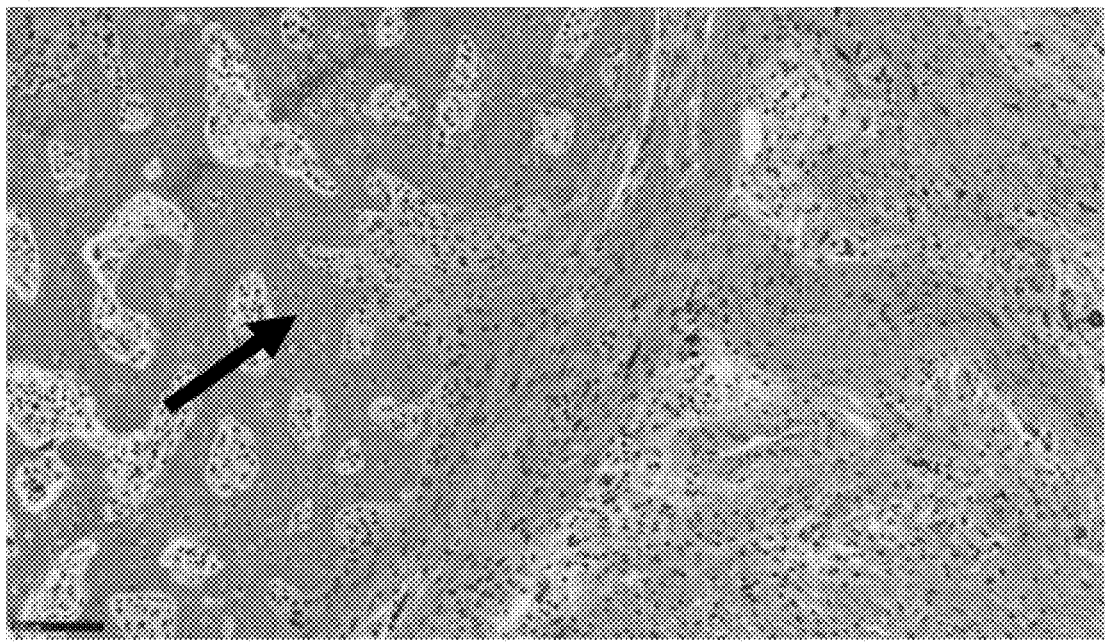
Figure 17A:
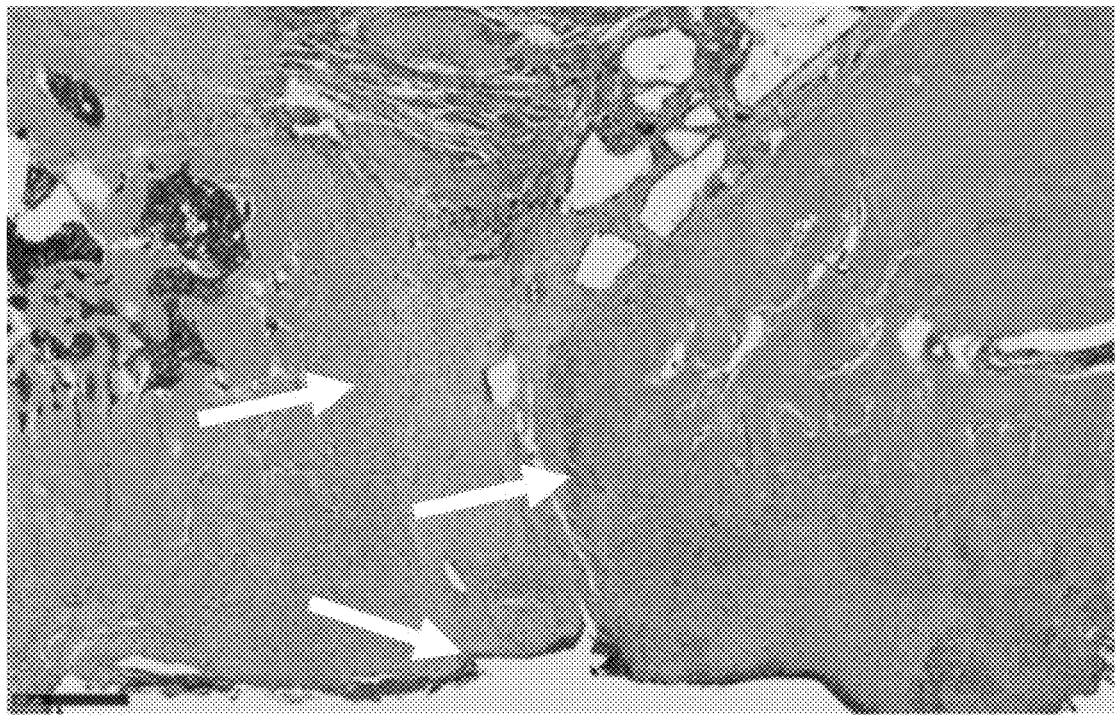
FIGS. 17A-17C are a set of photographs showing histology of bone defect 1 month after implantation of the biomaterial of the invention: haematoxylin-eosin staining, original magnification ×5 (FIG. 17A); Masson's trichrome staining, original magnification ×20 (FIG. 17B); HLA-I immunostaining, original magnification ×10 (FIG. 17C). White arrows represent the integration of the product and bone fusion. Black arrow represents endochondral ossification directly in contact between the native bone and the biomaterial revealing bone union process.
Figure 17B:
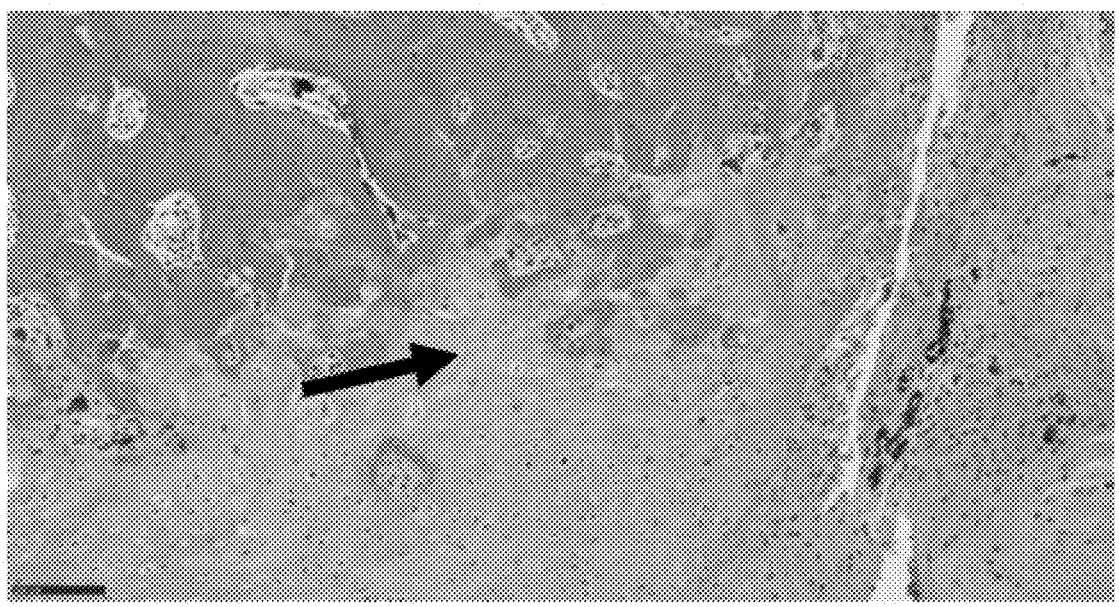
Figure 17C:
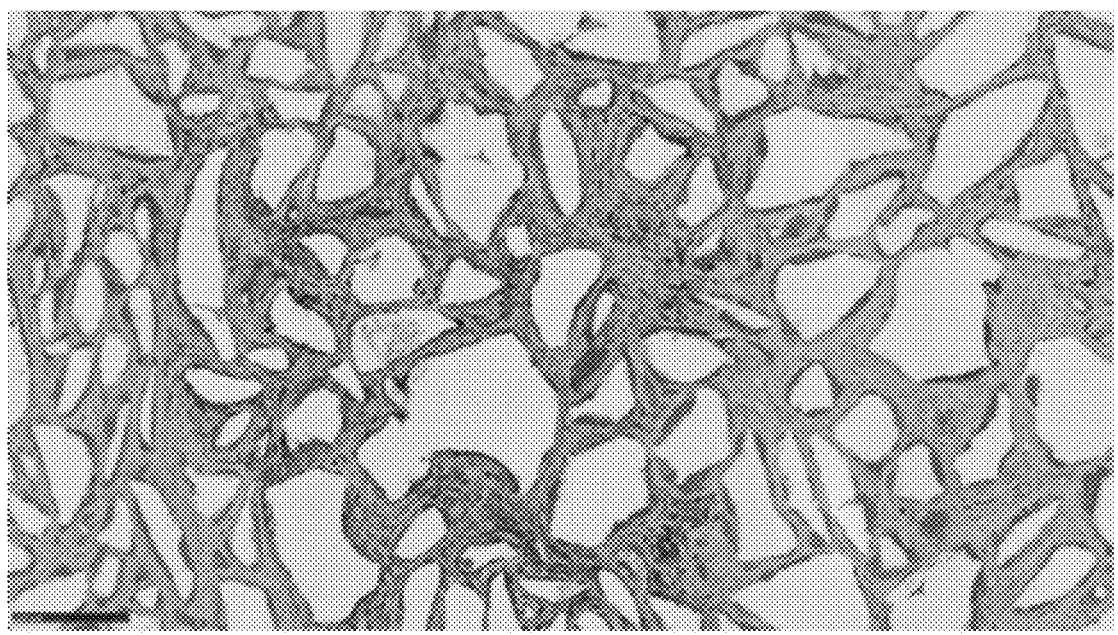

These results were confirmed by histology (FIGS. 16A-16B and 17A-17B). At 1-month post-implantation of HA/β-TCP particles alone, the product was not integrated and an important fibrosis was observed (FIG. 16A, white arrow). No endochondral ossification was found in the defect at the interface between the native bone and the implant of HA/β-TCP (FIG. 16B, black arrow). At 1-month post-implantation of the biomaterial of the invention, an integration of the product and bone fusion were observed (FIG. 17A, white arrows). Endochondral ossification was found directly in contact between the native bone and the biomaterial, revealing bone union process (FIG. 17B, black arrow). HLA-I staining reveals the presence of human cells (FIG. 17C).

These in vivo studies demonstrated (i) the capacity of the biomaterial of the invention to improve the osteogenicity in hypoxic environment and (ii) the capacity to perform a bone fusion in the context of a critical size bone defect. The biomaterial of the invention demonstrated its superiority in terms of osteogenicity and bone remodeling in comparison to HA/β-TCP particles alone.

Example 6: Study of the Biomaterial in a Spine Fusion Rat Model (Study CP-2017025-Biodistribution Arm)

Study Objective

A GLP-compliant study (Study CP-2017025) was performed pursuing the two-fold objective of assessing (i) the general toxicity of the biomaterial in a relevant animal model following conditions relevant to the intended clinical use of the investigation product (the so-called "CP-2017025-

Toxicology arm) and (ii) the biodistribution of the investigational cells and the potential consecutive development of ectopic tissues (the so-called "CP-2017025-Biodistribution arm).

An immune-deficient (nude) rat model was selected to avoid rejection of human cells as would be anticipated with immunocompetent animals. A spine fusion surgery model was chosen as a relevant model because it is well described in the literature (Wang et al., J. Bone and Joint Surg. 2003, 85:905-911) and it can accommodate larger implantation volumes than in a femoral bone defect (Belill et al., Comp. Med. 2014, 61(3):186-192) in similar tissue environments. In addition, the implantation environment created during the spine fusion chirurgical procedure has been considered very similar when compared to the environment created in bone non-union models such as femoral bone defects.

Study Design

For the purpose of the "Biodistribution study arm," twenty (20) healthy 9-week old homozygous nude athymic rats (10 males and 10 females; Hsd:RH-Foxn1 rnu/rnu) were randomly allocated in groups 1 and 2 (5 males and 5 females per group) (Table 2).

TABLE 2

Study (CP-2017025-Biodistribution arm) design

| Groups | Number of rats | Treatment | Dose | Administration route | Treatment schedule | Sacrifice |
|---|---|---|---|---|---|---|
| 1 | 5 males and 5 females | investigational biomaterial | $1.1 \times 10^7$ | Paravertebral: two sites | Q1D × 1 | D29 |
| 2 | 5 males and 5 females | sham operated | — | | | D29 |

Animals of group 1 were treated at D0 with the biomaterial (one batch manufactured according to the same process as for clinical batches) following the surgical procedure described below. Animals of group 2 were not treated with the biomaterial but underwent the same surgical procedure at D0 as the animals of group 1.

According to the surgical method described by Wang et al., the skin and muscles were cut open along the 5th or 6th lumbar vertebra. The dorsal muscles were split and separated allowing seeing lumbar vertebrae. A round bone defect was created in the transverse process of L5 lumbar vertebra. Bone defect size was standardized through the use of a constant diameter drill bit to control defect diameter at 2.0 mm, 1 mm deep. The two sides of lumbar vertebra were defected. For animals of group 1, the biomaterial (two pieces of 0.375 cm³ containing each $0.56 \times 10^7$ cells) was grafted on each side of the spine (left and right) in the created hole and in the surrounding area. The dorsal muscles and skin were then sutured. Based on rat body weight, this amount of the biomaterial represents a relative safety margin of 10 (for a rat of 250 g vs a patient of 30 kg) and 23.4 (for a rat of 250 g vs a patient of 70 kg).

At D29, rats were sacrificed and an autopsy was performed. For the purpose of detecting and quantifying the presence of the biomaterial human cells in rat tissues, total genomic DNA was extracted from the administration site, bone marrow, brain, gonads, heart, intestines, kidneys, liver, lungs, skeletal muscle and spleen, before being analyzed using a human Alu element-based qPCR method.

Organs were collected, weighed and kept at −80° C. until DNA extraction. Tissues were then wholly homogenized in extraction buffer by using a mechanical method followed by DNA extraction. qPCR experiments were carried out in 20 µl with either 125 ng of genomic DNA of test rat tissue sample or control rat tissue sample. Each sample was tested in triplicate. The Alu element-based qPCR method was validated for a range of quantification from 20 fg (lower limit of quantification for all organs) or 70 fg (lower limit of quantification for skeletal muscle) to 7 ng (upper limit of quantification) of human DNA spiked in 125 ng of specific tissue DNA matrix from rat.

Results

Human DNA was not detected at or below the limit of quantification in samples from bone marrow, brain, gonads, heart, intestines, kidneys, liver, lungs, skeletal muscle and spleen of animals of groups 1 and 2, and from administration sites of animals of group 2. Human DNA was detected in all administration sites of animals of group 1 and in the heart of 1 out of 10 animals of group 1.

In addition to all implantation sites of the biomaterial treated rats, human DNA was detected in the heart of 1 out of the 10 the biomaterial treated rats analyzed for biodistribution purpose. Even unexplained, this result may be due to a contamination during sampling, as it was observed only in one animal out of 10 analyzed, and since the amount of detected DNA was low (estimated number of human cells in the heart corresponding to 166 cells). In addition, histopathological analysis performed 29 days after implantation on hearts from the 10 the biomaterial treated rats did not evidence histopathological observations suggestive of ectopic tissue formation.

Example 7: Study of the Biomaterial in a Spine Fusion Rat Model (CP-2017025-Toxicology Arm)

Nonclinical toxicology for the biomaterial development was addressed through the following 3 animal studies including 2 GLP-compliant studies:

Single dose toxicity study of the biomaterial in a spine fusion rat model (GLP Study CP-2017025-Toxicology arm);

Tumorigenicity study of the biomaterial in NSG mice (GLP Study CP-2017026); and

Local tolerance study of the biomaterial in NSG mice with an investigation of tumor formation potential (CP-2017073).

Context and Objectives

A GLP-compliant study (Study CP-2017025) was performed pursuing the two-fold objective of assessing (i) the general toxicity of the biomaterial in a relevant animal model following conditions relevant to the intended clinical use of the investigation product (the so-called "CP-2017025-Toxicology arm) and (ii) the biodistribution of the investigational cells and the potential consecutive development of ectopic tissues (the so-called "CP-2017025-Biodistribution arm).

The objective of "Toxicology study arm" was to identify, characterize and quantify potential toxicities, their onset (acute or delayed) and the possibility for resolution of any observed toxicities.

An immune-deficient (nude) rat model was selected to avoid human cells rejection as would be anticipated with immunocompetent animals. A spine fusion surgery model was chosen as a relevant model because it is well described in the literature (Wang et al. 2003) and it can accommodate larger implantation volumes than in a femoral bone defect (Belill et al. 2014) in similar tissue environments. In addition, the implantation environment created during the spine fusion surgical procedure has been considered very similar when compared to the environment created in bone nonunion models such as femoral bone defects.

Study Design

For the purpose of the "Toxicity study arm," forty (40) healthy 9-week old Homozygous Nude athymic rats (20 males and 20 females; Hsd:RH-Foxn1 rnu/rnu) were randomly allocated in groups 1 and 2 (10 males and 10 females per group) (Table 3).

TABLE 3

Study (CP-2017025-Toxicology arm) design

| Groups | Number of rats | Treatment | Dose | Administration route | Treatment schedule | Sacrifice |
|---|---|---|---|---|---|---|
| 1 | 10 males and 10 females | investigational biomaterial | $1.1 \times 10^7$ | Paravertebral: two sites | Q1D × 1 | D29 |
| 2 | 10 males and 10 females | sham operated | — | | | D29 |

Animals of group 1 were treated at D0 with the biomaterial (one batch manufactured according to the same process as for clinical batches) following the surgical procedure described below. Animals of group 2 were not treated with the biomaterial but underwent at D0 a same surgical procedure than animals of group 1.

According to the surgical method described by Wang et al., the skin and muscles were cut open along the 5th or 6th lumbar vertebra. The dorsal muscles were split and separated allowing seeing lumbar vertebrae. A round bone defect was created in the transverse process of L5 lumbar vertebra. Bone defect size was standardized using a constant diameter drill bit to control defect diameter at 2.0 mm, 1 mm deep. The two sides of lumbar vertebrae were defected. For animals of group 1, the biomaterial (two pieces of 0.375 cm$^3$ containing each $0.56 \times 10^7$ cells) was grafted on each side of the spine (left and right) in the created hole and in the surrounding area. The dorsal muscles and skin were then sutured. Based on rat body weight, this amount of the biomaterial represents a relative safety margin of 10 (for a rat of 250 g vs a patient of 30 kg) and 23.4 (for a rat of 250 g vs a patient of 70 kg).

Rats were observed after the surgery for the post anesthesia recovery, then animals were monitored each day until D29 for wound healing, mobility, morbidity, mortality and evident sign of toxicity.

The body weight was measured for randomization purpose, and at D0, then at least twice a week. Weight evolution was assessed and compared between animals of groups 1 and 2.

At D3 and D29, blood from fasted rats of group 1 and 2 was collected to measure hematology, coagulation, and biochemistry parameters. At D29, rats were sacrificed, and an autopsy was performed.

For toxicity purpose, organs of 5 animals per sex per group were macroscopically observed and collected. Spleen, liver, kidneys and heart were weighed. All collected organs were preserved at room temperature in formalin 4%, paraffin embedded, and slides were generated (3 slides per organ; 20 animals) and analyzed microscopically.

Results

No relevant observation was reported during the monitoring period. In terms of body weights, no statistically significant difference in body weight was observed between animals of groups 1 and 2. From analyses performed on blood samples taken on days 3 and 29, no relevant difference was reported between animals of groups 1 and 2 for hematology, biochemistry and coagulation parameters. Macroscopically, nothing relevant was reported from the performed autopsies. Microscopically, foreign body granuloma, probably due to the biomaterial implantation, was observed at the implantation site of all animals of group 1. There were no other histopathological systemic changes which could be attributed to the biomaterial implantation.

In conclusion, no toxicity was evidenced following the biomaterial implantation using a relevant model in nude rats.

Example 8: Cell Transformation Risk Assessment

Substantial evidence is available in human to support the mesenchymal origin of a spectrum of sarcomas including osteosarcomas. However, MSCs have not been shown to undergo spontaneous transformation in vitro despite chromosomal abnormalities developing in long-term cultures (Aguilar et al., Stem Cells. 2007, 25(6):1586-1594; Bernardo et al., Cancer Res. 2007, 67(19):9142-9149; Xiao et al., Clin. Sarcoma Res. 2013, 3(1):10). These anomalies have been described and suggested to be a natural adaptation to the in vitro culture conditions not linked to an increased risk for transformation (Tarte et al., Blood. 2010, 115(8): 1549-1553).

The potential for spontaneous cell transformation of ASCs was assessed in vitro by studying the cytogenetic stability of the biomaterial drug substance by molecular karyotyping (aCGH/SNP method) during the manufacture of more than 3 development batches of the biomaterial produced with the process that is proposed for the clinical batches. Array comparative genomic hybridization (aCGH) in combination with high-density single nucleotide polymorphism (SNP) is as well-established molecular genotyping method to provide an alternative means of genome-wide screening for copy number alterations and the detection of clinically relevant chromosomal abnormalities and disorders without the encumbrance of requiring prior isolation of mitotic cells (Cooper et al., Nat. Genetics. 2011, 43(9):838-846; Slavotinek. A. M., Hum. Genetics. 2008, 124(1): 1-17).

Results indicate that during the manufacturing process and at the passage level corresponding to the release testing of the biomaterial drug substance, the hASCs appear cytogenetically stable.

In Vivo GLP Tumorigenicity Study of the Biomaterial in NSG Mice (Study CP-2017026)

Context and Objectives

In the case of MSC-derived cell therapy administration, no tumor formation in human patients has been observed to date, although the obtained results neither confirm nor exclude the risk for tumorigenicity in patients (Barkholt et al., Cytotherapy. 2013, 15(7):753-759).

The objective of study CP-2017026 was to evaluate the risk of cellular transformation of human adipose derived MSCs contained in the biomaterial with respect to their tumorigenicity potential for a period of up to 6 months after implantation in NSG (NOD scid gamma) immunodeficient mice. The HT-29 cell line, selected for its validated tumorigenicity, was used as a positive control.

Study Design

Thirty (30) healthy NSG female mice, 7 weeks old were included in this study. Mice were randomized in 2 groups (20 mice in group 1 and 10 mice in group 2). Animals of group 1 were implanted with the biomaterial (1 g (±1 cm$^3$) containing 1.5×10$^7$ cells) in the subcutaneous space via an incision (same batch used in study CP-2017025, which was manufactured according to the same process as for clinical batches). Animals of group 2 were inoculated by subcutaneous injection with HT-29 cells (10$^7$ cells/mouse in 200 μl of NaCl 0.9%).

The viability, behavior and body weight of mice were recorded twice per week until the end of the experiment. Each animal was observed and palpated twice per week for newly formed nodules at the administration site. Any newly formed nodule was measured. Mice of group 1 (treated with the biomaterial) were observed up to 6 months while mice of group 2 (treated with HT-29 cells) were monitored until tumor volume reaches 1000 mm$^3$ or until necrosis was ob served During autopsy, macroscopic observations were performed for each animal. For the group 1 animals (test item), slides for histopathological examination were prepared for implantation site, liver, spleen, lungs, heart, kidney, brain, inguinal lymph nodes (where visible).

Results

The 10 mice of group 2 (HT-29, positive control) have shown progressively growing tumors with a mean tumor volume (MTV) at D27 (day of the first sacrifice) of 611.6±335.4 mm$^3$. One mouse was sacrificed due to necrosis on the tumor and the 9 other mice were sacrificed for TV>1000 mm$^3$. Macroscopic observation of the organs performed during the autopsy of group 2 mice did not reveal abnormalities.

One mouse of group 1 lost the test item between D0 and D1 because of the opening of the suture at the administration site. For animals of group 1, mean volume of implantation site after implantation (D2) was 1194.6±392.7 mm$^3$ (N=19). After implantation, some mice presented severe wounds not healing at the level of the administration site.

As a consequence, 10 out of the 20 mice from group 1 were killed for ethical reasons between D3 and D27 because of these severe skin wounds at administration site. Among the 10 sacrificed mice from group 1, 5 mice presented dry and yellow skin at the implantation site and necrosis at the implantation site was observed in 2 other mice. Histopathological examination revealed inflammation at implantation site and the mass was sometimes necrotic. Inflammation and/or ulceration were observed in the overlying skin and surrounding muscular tissue.

The mean implantation site volume was 1032.5±245.3 (n=9) mm$^3$ at the end of the study (D180) for group 1 animals showing an absence of volume increase as compared to the mean volume of implantation site at D2.

Macroscopic observation of the organs performed during the autopsy of group 1 mice did not reveal abnormalities. For group 1 mice sacrificed at the end of the study (D180), microscopic observations revealed a multilocular mass at implantation site without necrosis and generally not accompanied by inflammation nearby tissues. No tumors were observed in any of the group 1 mice during the histopathological examination of the implantation sites and the other organs analyzed.

The study is valid since at least 9 out of 10 animals of group 2 (HT-29 cells treated) have shown progressively growing tumors. No tumors were observed in any of the group 1 (female NSG) mice after a single subcutaneous implantation of the test item (1 g of the biomaterial) containing around 1.5×10$^7$ cells.

The histopathology report indicated that under the conditions of this experiment, "the subcutaneous implantation of approximately 1 g of [the biomaterial] in NSG mice did not induce any cellular proliferation over a 6-month observation period. At the implantation site, a multilocular mass was present, directly related to the test item. In some mice, it led to premature sacrifice because of skin ulceration with local inflammatory reaction. This was considered to be related to the mechanical trauma caused by the subcutaneous implantation of a high volume of a hard material."

In Vivo Local Tolerance Study of the Biomaterial in NSG Mice with an Investigation of the Potential for Tumor Formation (Study CP-2017073)

Context and Objectives

During the GLP tumorigenicity study CP-2017026, a poor local tolerance of the biomaterial implant was observed and considered to be related to the mechanical trauma caused by the subcutaneous implantation in NSG immunodeficient mice of a high volume of a hard material.

Study CP-2017073 was initiated to further investigate the local tolerance (on a two week period, as per the original plan) of 1 g (±1 cm$^3$) of the biomaterial after implantation either in a single site (as performed in study CP-2017026) (n=8) or in two sites (0.5 g per site)(n=8).

Of note, during study CP-2017073 and in contrast to study CP-2017026, no animal implanted with 1 g of the biomaterial had to be sacrificed for ethical reasons because of severe skin wounds at administration site even if lesions (e.g. yellow skin at the implantation site without adhesion at the muscular level) were observed. It was then decided, in order to complement the tumorigenicity data already generated in study CP-2017026, to monitor the animals of group 1 (n=8) for a longer period (up to 6 months) than the 2 week follow-up period originally defined.

Study Design

Sixteen (16) healthy NSG (NOD scid gamma) immunodeficient female mice, 7 weeks old, were randomized in 2 groups (8 mice per group). Animals of group 1 were implanted with the biomaterial (1 g containing 1.5×10$^7$ cells) via an incision in the subcutaneous space of the right flank. Animals of group 2 were implanted with the biomaterial (2×0.5 g containing 0.75×10$^7$ cells on each site) via an incision in the subcutaneous space of the right and left flank. The viability, behavior and body weight of mice were recorded twice a week until the end of the experiment. Each animal was observed daily for clinical signs and local reactions. Mice of group 1 (treated with the test item at one site) were observed up to 6 months. Mice of group 2 (treated with the test item at two sites) were monitored for a period of 15 days. A macroscopic autopsy was performed for each animal. For the group 1 animals (test item), slides for histopathological examination were prepared for implantation site, liver, spleen, lungs, heart, kidney, brain, inguinal lymph nodes (where visible).

Results

Body weight of each mouse increased progressively from D0 until sacrifices except for one mouse of group 1 with body weight loss from D79 to D85. That mouse was found dead on D89.

For animals of group 1, mean volume of implantation sites on D2 was 1228.3±195.3 mm$^3$ (n=8). The mean implantation site volume decreased to 945.5±92.7 mm$^3$ (n=7) at the end of the study (D180) showing that, after subcutaneous implantation of the test item, no increase in size of any implantation site was observed during the study.

Monitoring parameters (mobility and gait, carriage, behavior, breathing, eyes, skin (other than at the implantation sites), fur, mucus membranes, excretions and no paralysis) were normal for all the mice of group 1 (one site) and group 2 (two sites).

At sacrifice, macroscopic observations performed on group 1 mice (one site) or group 2 (two sites) revealed no abnormal organs. For mice of group 1 sacrificed at D180, histopathological analysis did not evidence any cellular proliferation. Multilocular mineralization was observed at implantation site, but without inflammation in the overlying skin and the nearby muscular tissue. This mineralized material is interpreted to be the implanted test item.

Under the Conditions of this Experiment, it can be Concluded that:

Administration of the biomaterial in one or two sites had no significant effect on local tolerance even if yellow skin at the implantation site was observed in both groups. With respect to that observation, animals of group 1 recovered since the last observation of a yellow skin at implantation site was noticed at D44.

A single subcutaneous implantation of the biomaterial containing 1.5×10$^7$ cells did not induce tumor formation in female NSG mice as investigated macroscopically and microscopically after a 6-month follow-up.

The histopathology report indicated that the subcutaneous implantation of 1 g of the biomaterial containing 1.5×10$^7$ cells to NSG mice did not induce any cellular proliferation over a 6-month period. At the implantation site, multilocular mineralization was present, directly related to the test item.

The invention claimed is:

1. A three-dimensional biomaterial produced by a method for producing a scaffold-free three-dimensional biomaterial comprising the steps of:
   (a) isolating autologous adipose stem cells (ASCs) from a human subject;
   (b) proliferating the isolated ASCs in vitro;
   (c) differentiating the proliferated ASCs in vitro into an osteogenic cell phenotype;
   (d) adding particles comprising a mixture of hydroxyapatite (HA) and beta-tricalciumphosphate (B-TCP) homogenously to the surface of the osteogenic differentiated ASCs; and
   (e) culturing the osteogenic differentiated ASCs with the particles of calcium phosphate, thereby producing the scaffold-free three-dimensional biomaterial;
   wherein scaffold-free means essentially free of any exogenous extracellular matrix;
   wherein the biomaterial comprises an extracellular matrix (ECM) secreted by the ASCs;
   wherein the ASCs and the particles of HA and B-TCP are integrated into the ECM;
   wherein the biomaterial secretes at least about 5 ng of osteoprotegerin (OPG) per g of biomaterial.

2. The three-dimensional biomaterial of claim 1, wherein the biomaterial is moldable or formable.

3. The three-dimensional biomaterial of claim 1, wherein the biomaterial secretes at least about 10 ng of OPG per g of biomaterial.

4. The three-dimensional biomaterial of claim 1, wherein the biomaterial comprises at least about 50 ng of insulin-like growth factor (IGF I) per g of biomaterial.

5. The three-dimensional biomaterial of claim 1, wherein the biomaterial comprises at least about 75 ng of IGF1 per g of biomaterial.

6. The three-dimensional biomaterial of claim 1, wherein the biomaterial comprises at most about 100 ng of stromal cell-derived factor I-alpha (SDF1a) per g of biomaterial.

7. The three-dimensional biomaterial of claim 1, wherein the biomaterial is osteoinductive.

8. The three-dimensional biomaterial of claim 1, wherein the biomaterial is angiogenic.

9. The three-dimensional biomaterial of claim 1, wherein the biomaterial is vascularized.

10. The three-dimensional biomaterial of claim 1, wherein the biomaterial is characterized by mineralization surrounding the particles of HA and B-TCP.

* * * * *